(12) United States Patent
Bateman et al.

(10) Patent No.: US 7,586,088 B2
(45) Date of Patent: Sep. 8, 2009

(54) MASS SPECTROMETER AND METHOD OF MASS SPECTROMETRY

(75) Inventors: Robert Harold Bateman, Knutsford (GB); John Brian Hoyes, Stockport (GB); James Ian Langridge, Sale (GB); Jason Lee Wildgoose, Heaton Mersey (GB)

(73) Assignee: Micromass UK Limited, Manchester (GB)

(*) Notice: Subject to any disclaimer, the term of this patent is extended or adjusted under 35 U.S.C. 154(b) by 1480 days.

(21) Appl. No.: 10/176,072

(22) Filed: Jun. 21, 2002

(65) Prior Publication Data

US 2003/0001084 A1   Jan. 2, 2003

Related U.S. Application Data

(60) Provisional application No. 60/299,771, filed on Jun. 22, 2001, provisional application No. 60/361,112, filed on Mar. 1, 2002.

(30) Foreign Application Priority Data

Jun. 21, 2001  (GB) ................................. 0115203.2

(51) Int. Cl.
    *H01J 49/26* (2006.01)
(52) U.S. Cl. ........................ 250/281; 250/287
(58) Field of Classification Search ............... 250/281
    See application file for complete search history.

(56) References Cited

U.S. PATENT DOCUMENTS

| | | | |
|---|---|---|---|
| 5,140,158 A | | 8/1992 | Post |
| 5,552,600 A | * | 9/1996 | Davies et al. ............... 250/286 |
| 5,789,745 A | | 8/1998 | Martin et al. |
| 5,818,055 A | * | 10/1998 | Franzen ..................... 250/292 |
| 6,020,586 A | * | 2/2000 | Dresch et al. ............... 250/287 |
| 6,124,592 A | | 9/2000 | Spangler |
| 6,188,066 B1 | * | 2/2001 | Whitehouse et al. ........ 250/288 |
| 6,498,342 B1 | * | 12/2002 | Clemmer ..................... 250/287 |
| 2002/0014586 A1 | * | 2/2002 | Clemmer ..................... 250/287 |
| 2002/0070338 A1 | * | 6/2002 | Loboda ....................... 250/287 |
| 2002/0070339 A1 | | 6/2002 | Clemmer |
| 2003/0038235 A1 | * | 2/2003 | Guevremont et al. ....... 250/287 |

(Continued)

FOREIGN PATENT DOCUMENTS

EP   1102986   5/2001

(Continued)

OTHER PUBLICATIONS

Liu et al., "Injected-Ion Mobility Analysis of Biomolecules", Analytical Chemistry News & Features, pp. 728 A-735 A, Dec. 1, 1997, pp. 728 A-735 A.

(Continued)

*Primary Examiner*—David A. Vanore
*Assistant Examiner*—Phillip A. Johnston
(74) *Attorney, Agent, or Firm*—Diederiks & Whitelaw, PLC

(57) ABSTRACT

A mass spectrometer is disclosed comprising an ion mobility spectrometer in combination with a quadrupole mass filter which is scanned in synchronization with the pulsing of ions into the ion mobility spectrometer thereby enabling ions having a particular charge state to be preferentially transmitted. Another embodiment replaces the quadrupole mass filter with an axial time of flight mass filter and an injection electrode.

54 Claims, 12 Drawing Sheets

U.S. PATENT DOCUMENTS

2003/0047681 A1* 3/2003 Guevremont et al. ....... 250/288

FOREIGN PATENT DOCUMENTS

| GB | 2217103 | 10/1989 |
| --- | --- | --- |
| WO | WO 97/07530 | 2/1997 |
| WO | WO 98/56029 | 12/1998 |
| WO | WO 00/08455 | 2/2000 |
| WO | WO 00/08456 | 2/2000 |
| WO | WO 00/70335 | 11/2000 |
| WO | 01/35441 | 5/2001 |
| WO | 01/69221 | 9/2001 |
| WO | WO 01/64320 A1 | 9/2001 |
| WO | WO 01/69218 | 9/2001 |
| WO | WO 01/69220 | 9/2001 |
| WO | WO 01/69647 | 9/2001 |
| WO | WO 02/07185 | 1/2002 |

OTHER PUBLICATIONS

Purves et al., "Mass Spectrometric Characterization of a High-Field Asymmetric Waveform Ion Mobility Spectrometer", Review of Scientific Instruments, vol. 69, No. 12, pp. 4094-4105.

Purves et al., "Electrospray Ionization High-Field Asymmetric Waveform Ion Mobility Spectrometry-Mass Spectrometry", Analytical Chemistry, vol. 71, No. 13, Jul. 1, 1999, pp. 2346-2357.

Hoaglund et al., "Three-Dimensional Ion Mobility/TOFMS Analysis of Electrosprayed Biomolecules", Analytical Chemistry, vol. 70, No. 11, Jun. 1, 1998, pp. 2236-2242.

Griffin et al., "Ion Mass Assignments Based on Mobility Measurements", Analytical Chemistry, vol. 45, No. 7, Jun. 1973, pp. 1204-1209.

Valentine et al., "Multidimensional Separations of Complex Peptide Mixtures: A Combined High-Performance Liquid Chromatography/Ion Mobility/Time-of-Flight Mass Spectrometry Approach", Int'l. J. of Mass Spectrometry 212, 2001, pp. 97-109.

Steiner et al., "Electrospray Ionization With Ambient Pressure Ion Mobility Separation and Mass Analysis By Orthogonal Time-Of-Flight Mass Spectrometry", Rapid Communications in Mass Spectrometry 2001; 15:, pp. 2221-2226.

Barnes et al., "Resolving Isomeric Peptide Mixtures: A Combined HPLC/Ion Mobility-TOFMS Analysis of a 4000-Component Combinatorial Library", Analytical Chemistry, vol. 74, No. 1, Jan. 1, 2002, pp. 26-36.

Srebalus et al., "Gas-Phase Separations of Electrosprayed Peptide Libraries", Analytical Chemistry, vol. 71, No. 18, Sep. 15, 1999, pp. 3918-3927.

Villinger et al., "An Evaluati n of the Role of Internal Energy and Translational Energy in the Endothermic Proton Transfer Reaction of $N_2H^+$ with Kr", J. Chem. Phys., vol. 80, No. 6, Mar. 15, 1984, pp. 2543-2547.

Kolaitis et al., "Atmospheric Pressure Ionization Mass Spectrometry With Laser-Produced Ions", Analytical Chemistry, vol. 58, No. 9, Aug. 1986, pp. 1993-2001.

Eiceman et al., "A Micro-Machines Ion Mobility Spectrometer-Mass Spectrometer", IJIMS 3 (2000)1, 15-27, pp. 15-27.

Hoaglund-Hyzer et al., "Mobility Labeling For Parallel CID of Ion Mixtures", Analytical Chemistry, vol. 72, No. 13, Jul. 1, 2000, pp. 2737-2740.

Hoaglund-Hyzer et al., "Ion Trap/Ion Mobility/Quadrupole/Time-of-Flight Mass Spectrometry for Peptide Mixture Analysis", Analytical Chemistry, vol. 73, No. 2, Jan. 15, 2001, pp. 177-184.

Barnes et al., "Assessment of Purity and Screening of Peptide Libraries by Nested Ion Mobility-TOFMS: Identification of Rnase S-Protein Binders", Analytical Chemistry, vol. 73, No. 3, Feb. 1, 2001, pp. 424-433.

Badman et al., "Monitoring Structural Changes of Proteins in an Ion Trap over~10-200 ms: Unfolding Transitions in Cytochrome c Ions", Analytical Chemistry, vol. 73, No. 24, Dec. 15, 2001, pp. 6000-6007.

Henderson et al., "ESI/Ion Trap/Ion Mobility/Time-of-Flight Mass Spectrometry for Rapid and Sensitive Analysis of Biomolecular Mixtures", Analytical Chemistry, vol. 71, No. 2, Jan. 15, 1999, pp. 291-301.

Hoaglund et al., "An Ion Trap Interface for ESI-Ion Mobility Experiments", Analytical Chemistry, vol. 69, No. 20, Oct. 15, 1997, pp. 4156-4161.

Valentine et al., "Gas-Phase Separations of Protease Digests", American Society for Mass Spectrometry, No. 9, 1998, pp. 1213-1216.

Guevremont et al., "Ion Trapping at Atmospheric Pressure (760 Torr) and Room Temperature With a High-Field Asymmetric Waveform Ion Mobility Spectrometry", Int'l. Journal of Mass Spectrometry, vol. 193, (1999), pp. 45-56.

Javahery et al., "A Segmented Radiofrequency-Only Quadrupole Collision Cell for Measurements of Ion Collision Cross Section on a Triple Quadrupole Mass Spectrometer", Journal of American Society for Mass Spectrometry, 1997, No. 8, pp. 697-702.

Guevremont et al., "Combined Ion Mobility/Time-of-Flight Mass Spectrometry Study of Electrospray-Generated Ions", Analytical Chemistry, vol. 69, No. 19, Oct. 1, 1997, pp. 3959-3965.

Schwager et al., "The Solitron—A New Spectrometer That Uses the Mass Selectivity of a Solitary, Traveling Electric Potential Hill", $42^{nd}$ ASMS Conference on Mass Spectrometry, pp. 512, 1994.

* cited by examiner

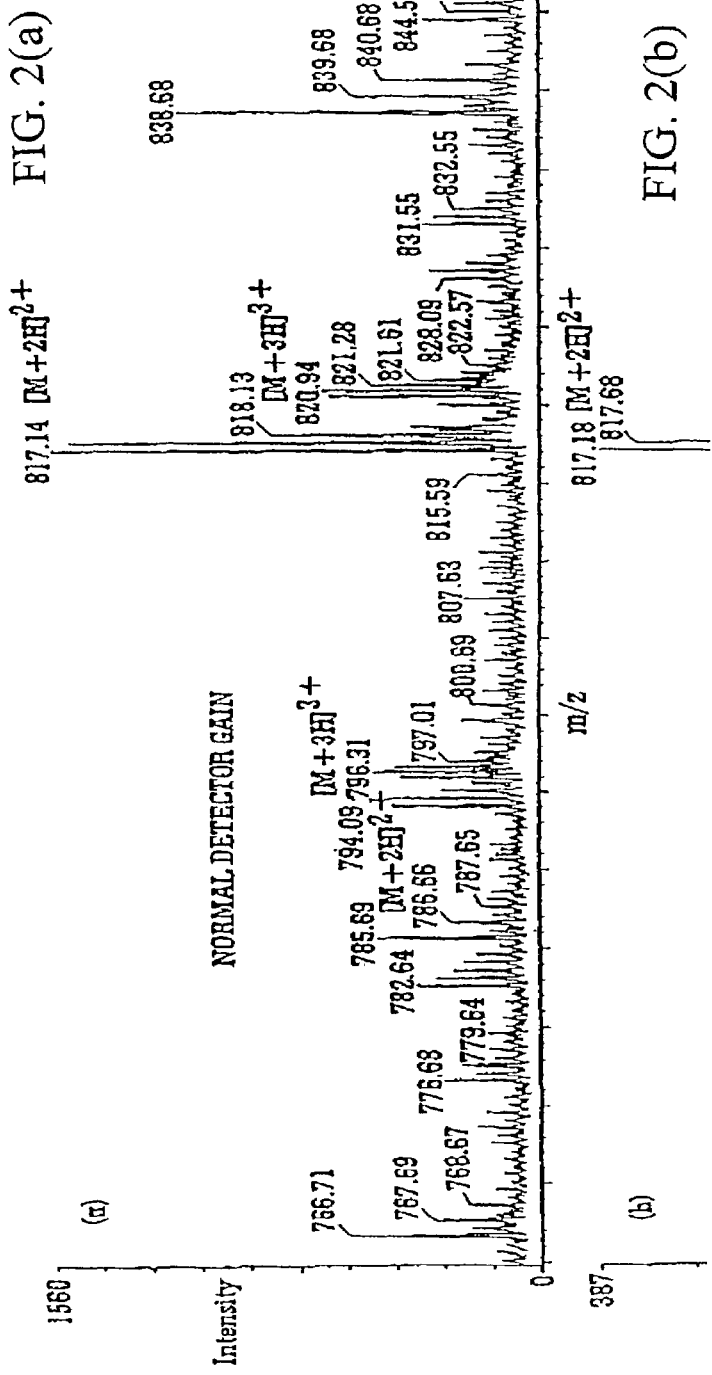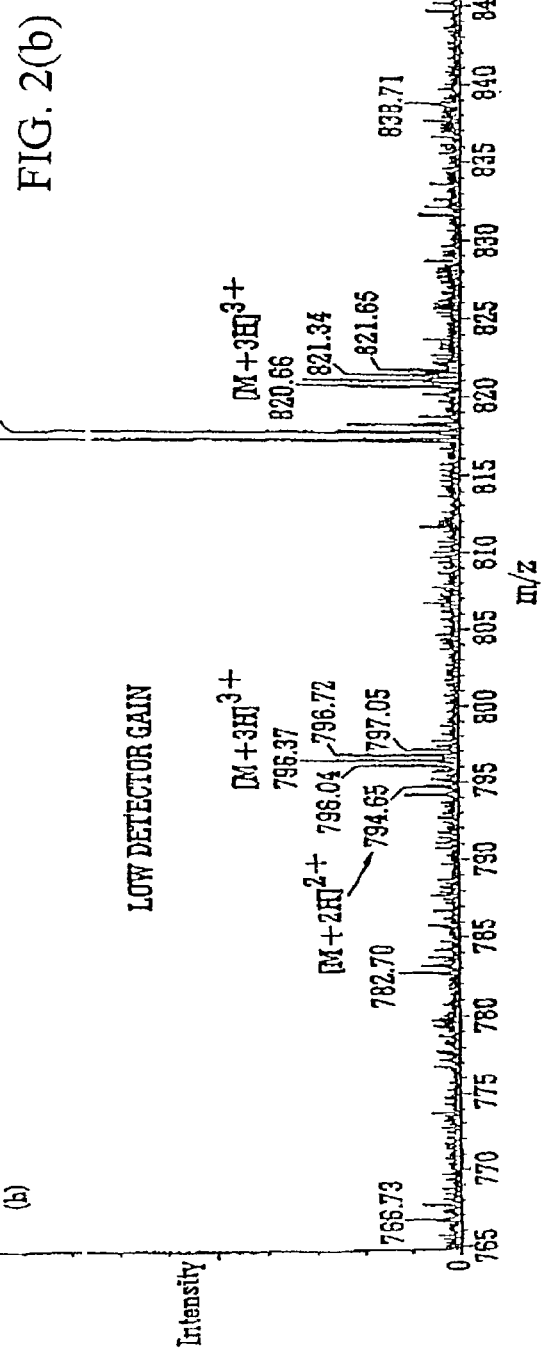
FIG. 2(a)
FIG. 2(b)

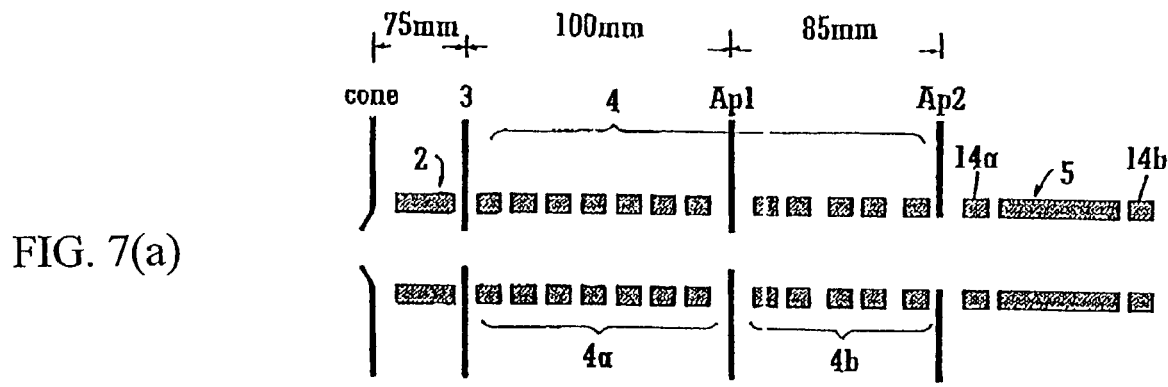
FIG. 7(a)
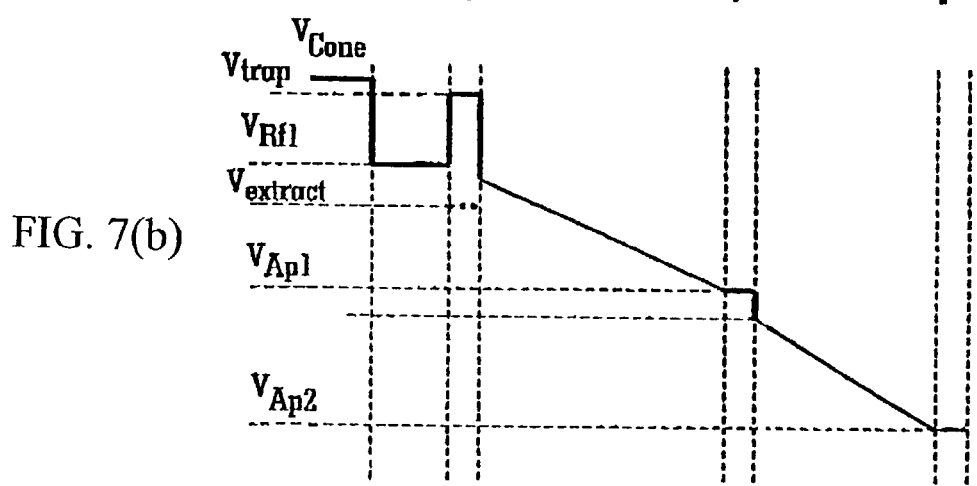
FIG. 7(b)
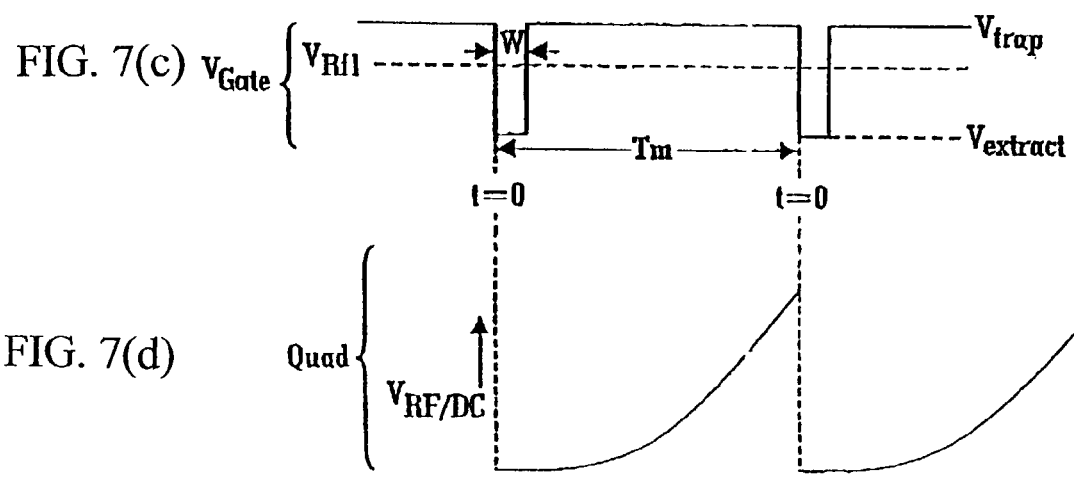
FIG. 7(c)
FIG. 7(d)

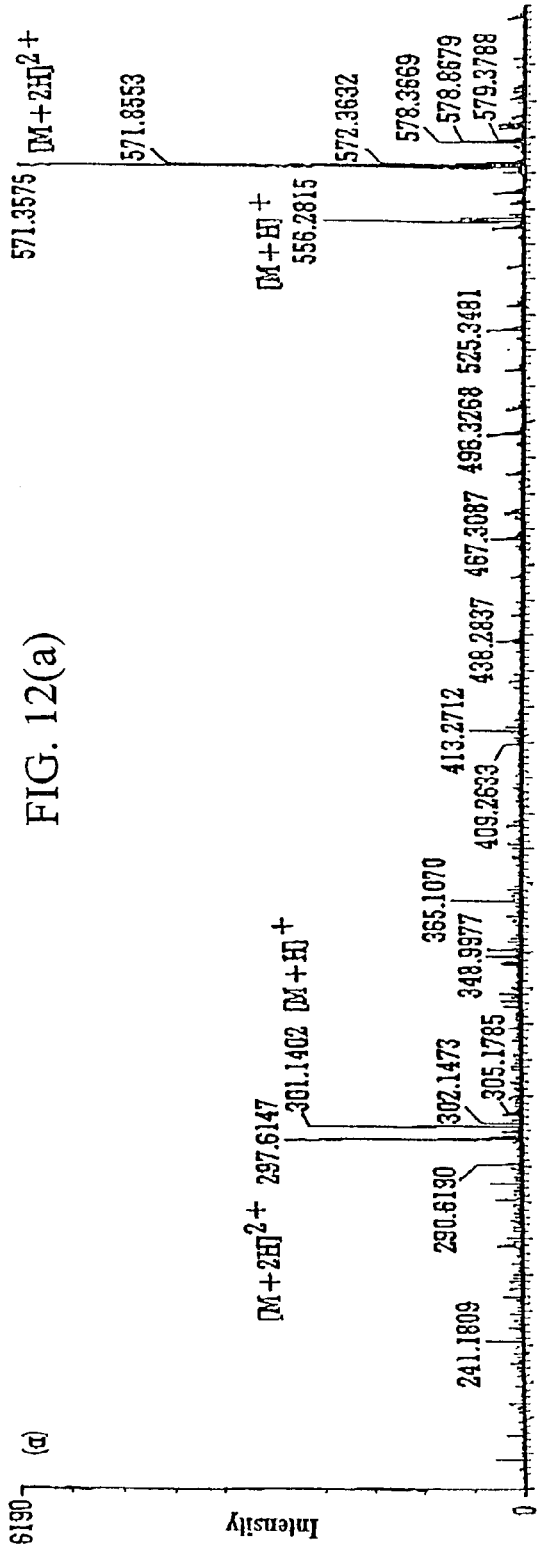
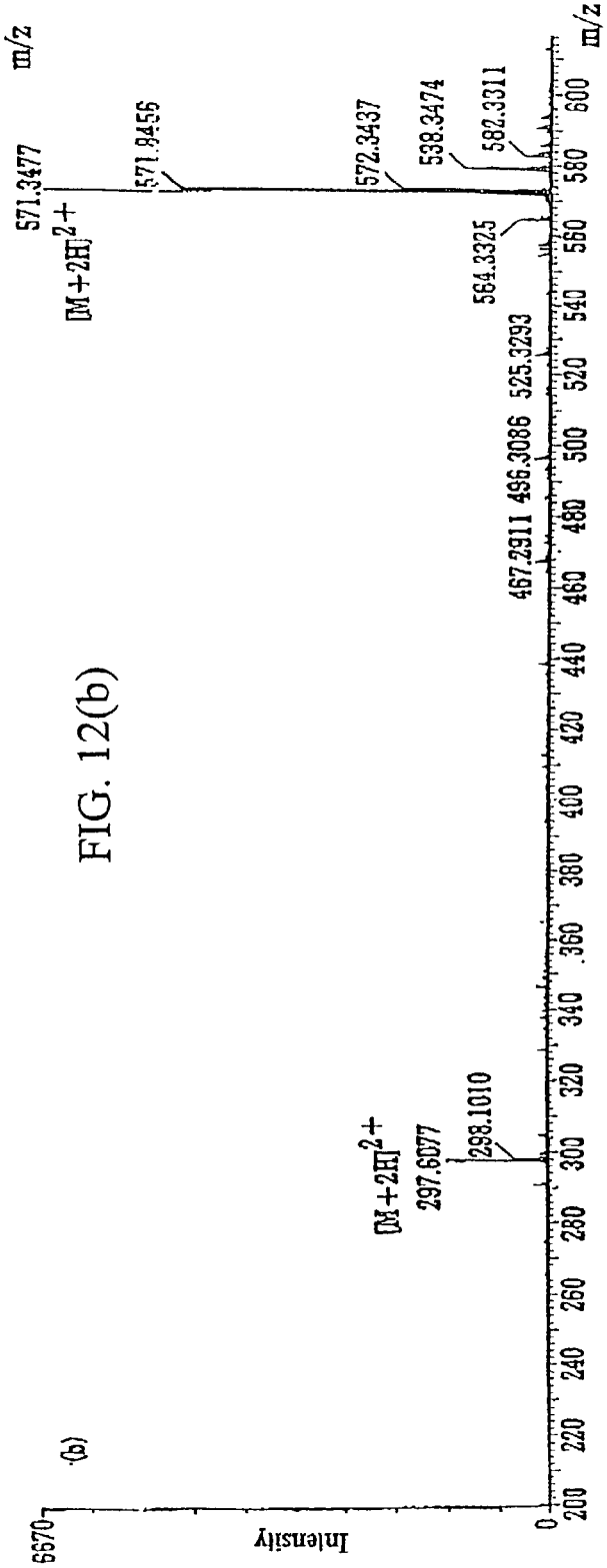
FIG. 12(a)
FIG. 12(b)

MASS SPECTROMETER AND METHOD OF MASS SPECTROMETRY

CROSS-REFERENCE TO RELATED APPLICATIONS

This application claims the benefit of U.S. Provisional Application Serial No. 60/299,771 filed Jun. 22, 2001 and U.S. Provisional Application Serial No. 60/361,112 filed Mar. 1, 2002.

BACKGROUND OF THE INVENTION

With the decoding of the 20-30,000 genes that compose the human genome, emphasis has switched to the identification of the translated gene products that comprise the proteome. Mass spectrometry has firmly established itself as the primary technique for identifying proteins due to its unparalleled speed, sensitivity and specificity. Strategies can involve either analysis of the intact protein, or more commonly digestion of the protein using a specific protease that cleaves at predictable residues along the peptide backbone. This provides smaller stretches of peptide sequence that are more amenable to analysis via mass spectrometry.

The mass spectrometry technique providing the highest degree of specificity and sensitivity is Electrospray ionisation ("ESI") interfaced to a tandem mass spectrometer. These experiments involve separation of the complex digest mixture by microcapillary liquid chromatography with on-line mass spectral detection using automated acquisition modes whereby conventional MS and MS/MS spectra are collected in a data dependant manner. This information can be used directly to search databases for matching sequences leading to identification of the parent protein. This approach can be used to identify proteins that are present at low endogenous concentrations. However, often the limiting factor for identification of the protein is not the quality of the MS/MS spectrum produced but is the initial discovery of the multiply charged peptide precursor ion in the MS mode. This is due to the level of background chemical noise, largely singly charged in nature, which may be produced in the ion source of the mass spectrometer. FIG. 1 shows a typical conventional mass spectrum and illustrates how doubly charged species may be obscured amongst a singly charged background. A method whereby the chemical noise is reduced so that the mass spectrometer can more easily target peptide related ions would be highly advantageous for the study of protein digests.

A known method used to favour the detection of multiply charged species over singly charged species is to use an Electrospray ionisation orthogonal acceleration time of flight mass analyser ("ESI-oaTOF"). The orthogonal acceleration time of flight mass analyser counts the arrival of ions using a Time to Digital Converter ("TDC") which has a discriminator threshold. The voltage pulse of a single ion must be high enough to trigger the discriminator and so register the arrival of an ion. The detector producing the voltage may be an electron multiplier or a Microchannel Plate detector ("MCP"). These detectors are charge sensitive so the size of signal they produce increases with increasing charge state. Discrimination in favour of higher charge states can be accomplished by increasing the discriminator voltage level, lowering the detector gain, or a combination of both. FIG. 2(a) shows a mass spectrum obtained with normal detector gain and FIG. 2(b) shows a comparable mass spectrum obtained with a reduced detector gain. An important disadvantage of lowering the detector gain (or of increasing the discriminator level) is that the sensitivity is lowered. As can be seen from the ordinate axes of FIGS. 2(a) and (b), the sensitivity is reduced by a factor of ~x4 when a lower detector gain is employed. Using this method it is also impossible to pick out an individual charge state. Instead, the best that can be achieved is a reduction of the efficiency of detection of lower charge states with respect to higher charge states.

Another ionisation technique that has been recently coupled to tandem mass spectrometers for biological mass spectrometry is Matrix Assisted Laser Desorption Ionisation ("MALDI"). When a MALDI ion source is used high levels of singly charged matrix related ions and chemical noise are generated which make it difficult to identify candidate peptide ions.

SUMMARY OF THE INVENTION

It is therefore desired to provide an improved mass spectrometer and method of mass spectrometry which does not suffer from some or all of the disadvantages of the prior art.

According to a first aspect of present invention there is provided a method of mass spectrometry comprising: providing a pulse of ions and performing the following steps before providing another pulse of ions: (a) temporally separating at least some of the ions according to their ion mobility in a first device; (b) mass filtering at least some of the ions according to their mass to charge ratio in a second device; and (c) progressively varying a mass filtering characteristic of the second device so that ions having a first charge state are onwardly transmitted in preference to ions having a second different charge state.

The preferred embodiment is particularly advantageous in that it allow ions with a chosen charge state to be selected from a mixture of ions having differing charge states. Another advantage is that sensitivity for this technique is greater than the known discriminator level technique as the detector can be run at full gain and all ions present may be counted.

According to the preferred embodiment, multiply charged ions (which may include doubly, triply and quadruply charged ions and ions having five or more charges) may be preferentially selected and transmitted whilst the intensity of singly charged ions may be reduced. In other embodiments any desired charged state or states may be selected. For example, two or more multiply charged states may be transmitted.

The first device preferably comprises an ion mobility spectrometer or other ion mobility device. Ions in an ion mobility spectrometer may be subjected to an electric field in the presence of a buffer gas so that different species of ion acquire different velocities and are temporally separated according to their ion mobility. The mobility of an ion in an ion mobility spectrometer typically depends inter alia upon its mass and its charge. Heavy ions with one charge tend to have lower mobilities than light ions with one charge. Also an ion of a particular mass to charge ratio with one charge tends to have a lower mobility than an ion with the same mass to charge ratio but carrying two (or more) charges.

The ion mobility spectrometer may be similar to a known ion mobility spectrometer comprising a drift tube together with one or more electrodes for maintaining an axial DC voltage gradient along at least a portion of the drift tube. Alternatively, the ion mobility spectrometer may comprise a Field Asymmetric Ion Mobility Spectrometer ("FAIMS"). In one embodiment a FAIMS may comprise two axially aligned inner cylinders surrounded by a long outer cylinder. The outer cylinder and a shorter inner cylinder are preferably held at the same electrical potential. A longer inner cylinder may have a high frequency high voltage asymmetric waveform applied to it, thereby establishing an electric field between the inner and outer cylinders. A compensation DC voltage is also applied to the longer inner cylinder. A FAIMS acts like a mobility filter and may operate at atmospheric pressure.

However, according to a particularly preferred embodiment, a new form of ion mobility spectrometer is contemplated comprising a plurality of electrodes having apertures wherein a DC voltage gradient is maintained across at least a portion of the ion mobility spectrometer and at least some of the electrodes are connected to an AC or RF voltage supply. The new form of ion mobility spectrometer is particularly advantageous in that the addition of an AC or RF voltage to the electrodes (which may be ring like or otherwise annular) results in radial confinement of the ions passing through the ion mobility spectrometer. Radial confinement of the ions results in higher ion transmission compared with conventional ion mobility spectrometers of the drift tube type.

The second device may preferably take one of two main forms. The first main preferred embodiment uses a quadrupole rod set mass filter and the second main preferred embodiment uses an axial time of flight drift region and a synchronised pusher electrode.

With regards the first main preferred embodiment, the quadrupole mass filter may be operated as a high pass mass to charge ratio filter so as to transmit substantially only ions having a mass to charge ratio greater than a minimum value. In this embodiment multiply charged ions can be preferentially transmitted compared to singly charged ions (i.e. doubly, triply, quadruply and ions having five or more charges may be transmitted whilst singly charged ions are attenuated).

According to another embodiment, the quadrupole mass filter may be operated as a band pass mass to charge ratio filter so as to substantially transmit only ions having a mass to charge ratio greater than a minimum value and smaller than a maximum value. This embodiment is particularly advantageous in that multiply charged ions of a single charge state e.g. triply charged, may be preferentially transmitted whilst ions having any other charge state are relatively attenuated. However, according to another embodiment ions having two or more neighbouring charge states (e.g. doubly and triply charged ions) may be transmitted and all other charge states may be attenuated. Embodiments are also contemplated wherein non-neighbouring charge states are selected (e.g. doubly and quadruply charged ions).

The quadrupole mass filter is preferably scanned so that the minimum mass to charge ratio cut-off is progressively increased during a cycle (which is defined as the period between consecutive pulses of ions being admitted into the ion mobility spectrometer). The quadrupole mass filter may be scanned in a substantially continuous (i.e. smooth) manner or alternatively the quadruple mass filter may be scanned in a substantially stepped manner.

According to the second main preferred embodiment, the second device may comprise a drift region, preferably free of any buffer gas and preferably an axial drift region, having an axis and an injection electrode for injecting at least some ions in a direction substantially orthogonal to the axis. The injection electrode may comprise a pusher and/or puller electrode of an orthogonal acceleration time of flight mass analyser.

A particularly preferred feature is to provide an ion trap upstream of the drift region. This ion trap is separate to an ion trap which may be provided preferably upstream of the ion mobility spectrometer. The ion trap may preferably store and periodically release ions so that a pulsed (rather than a continuous) source of ions is admitted or otherwise inputted in to the drift region. The injection electrode is arranged to inject ions a predetermined period of time after ions have first been released from the ion trap upstream of the drift region. The period of time is set so that only ions having a desired mass to charge ratio or a mass to charge ratio within a desired range are substantially injected by the injection electrode in an orthogonal direction and are hence onwardly transmitted.

In a preferred embodiment a single packet of ions is released from the ion trap and then the predetermined time delay is slightly increased. The process of increasing the time delay may be repeated a number of times (e.g. 40-50 times) during one cycle of ions being input into the ion mobility spectrometer.

According to another embodiment, a number of packets of ions (e.g. 4-5 packets) may be repeatedly released from the ion trap before the predetermined time delay is progressively increased. As with the other embodiment, the process of increasing the time delay may be repeated a number of times during one cycle.

At the upstream end of the mass spectrometer, the ion source may be a pulsed ion source such as a Matrix Assisted Laser Desorption Ionisation ("MALDI") ion source. The pulsed ion source may alternatively comprise a Laser Desorption Ionisation ion source which is not matrix assisted.

Alternatively, and more preferably, a continuous ion source may be used in which case an ion trap for storing ions and periodically releasing ions is also preferably provided. Continuous ion sources which may be used include Electrospray, Atmospheric Pressure Chemical Ionisation ("APCI"), Electron Impact ("EI"), Atmospheric Pressure Photon Ionisation ("APPI") and Chemical Ionisation ("CI") ion sources. Other continuous or pseudo-continuous ion sources may also be used. In an embodiment the mass spectrometer may be a Fourier Transform mass spectrometer or a Fourier Transform Ion Cyclotron Resonance mass spectrometer.

A collision cell may be provided in both the main preferred embodiments. In one mode of operation at least some ions entering the collision cell are caused to fragment.

An orthogonal acceleration time of flight mass analyser is particularly preferred for both main preferred embodiments, although another type of mass analyser such as a quadrupole mass analyser or a 3D ion trap are also contemplated.

According to a second aspect of the present invention, there is provided a method of mass spectrometry comprising: providing a pulse of ions; separating at least some of the ions according to their ion mobility in an ion mobility spectrometer; using a mass filter having a variable mass to charge ratio cutoff to mass filter at least some of the ions; and progressively increasing the mass to charge ratio cutoff in synchronisation with the ion mobility spectrometer.

According to a third aspect of the present invention, there is provided a method of mass spectrometry comprising: separating at least some ions according to their ion mobility; mass filtering at least some ions; and arranging for multiply charged ions to be transmitted and for singly charged ions to be attenuated.

According to a fourth aspect of the present invention, there is provided a method of reducing unwanted singly charged ions from a mass spectrum, comprising: separating ions in an ion mobility spectrometer; passing the ions to a mass filter; and arranging the mass filter to have a mass to charge ratio cut-off which increases in time, the cut-off being predetermined based upon the known drift times of singly and doubly charged ions through the ion mobility spectrometer.

According to a fifth aspect of the present invention, there is provided a method of mass spectrometry, comprising: providing a pulse of ions; temporally separating at least some of the ions according to their ion mobility in an ion mobility spectrometer; providing a quadrupole rod set mass filter; and progressively increasing a mass to charge ratio cut-off of the mass filter so that multiply charged ions are onwardly transmitted in preference to singly charged ions.

According to a sixth aspect of the present invention, there is provided a method of mass spectrometry, comprising: providing a pulse of ions; temporally separating at least some of the ions according to their ion mobility in an ion mobility spectrometer; providing a drift region and an injection electrode; repeatedly pulsing ions into the drift region and causing the injection electrode to inject at least some of the ions in a substantially orthogonal direction after a delay time; and repeatedly increasing the delay time; wherein multiply charged ions are onwardly transmitted in preference to singly charged ions.

According to a seventh aspect of the present invention, there is provided a mass spectrometer comprising: a first device for temporally separating ions according to their ion mobility; a second device for mass filtering at least some of the ions according to their mass to charge ratio; and a controller which is arranged to progressively vary a mass filtering characteristic of the second device so that ions having a first charge state are onwardly transmitted in preference to ions having a second charge state.

According to an eighth aspect of the present invention, there is provided a mass spectrometer comprising: an ion mobility spectrometer; a quadrupole mass filter; and control means for progressively increasing the mass to charge ratio cut-off of the quadrupole mass filter in synchronisation with the ion mobility spectrometer.

According to a ninth aspect of the present invention, there is provided a mass spectrometer comprising: an ion source; an ion mobility spectrometer for separating ions according to both their mass and charge state; a mass filter; control means for controlling the ion mobility spectrometer and the mass filter; and a mass analyser; wherein the control means is arranged to control the ion mobility spectrometer and the mass filter to attenuate ions having a first charge state so that there is a higher proportion of ions having a second charge state to ions having the first charge state downstream of the ion mobility spectrometer and the mass filter compared with upstream of the ion mobility spectrometer and the mass filter.

According to a tenth aspect of the present invention, there is provided a mass spectrometer comprising: an ion source; a mass filter; an ion mobility spectrometer arranged downstream of the mass filter; and a mass analyser; wherein the mass filter and the ion mobility spectrometer are operated, in use, so that doubly and/or other multiply charged ions are transmitted to the mass analyser and singly charged ions are attenuated.

According to an eleventh aspect of the present invention, there is provided a mass spectrometer comprising: a continuous ion source; a first ion trap; an ion mobility spectrometer downstream of the first ion trap, the ion mobility spectrometer comprising a plurality of electrodes having apertures therein through which ions may be transmitted, wherein in use a DC voltage gradient is maintained across at least a portion of the ion mobility spectrometer and at least some of the electrodes are supplied with an AC or RF voltage, and wherein at least some of the electrodes are housed in a vacuum chamber maintained in use at a pressure within the range 0.1-10 mbar; a quadrupole mass filter downstream of the ion mobility spectrometer; and an orthogonal time of flight mass analyser comprising a pusher and/or puller electrode, orthogonal drift region and detector, the orthogonal time of flight mass analyser being arranged downstream of the quadrupole mass filter.

According to a twelfth aspect of the present invention, there is provided a mass spectrometer comprising: a continuous ion source; a first ion trap; an ion mobility spectrometer downstream of the first ion trap, the ion mobility spectrometer comprising a plurality of electrodes having apertures therein through which ions may be transmitted, wherein in use a DC voltage gradient is maintained across at least a portion of the ion mobility spectrometer and at least some of the electrodes are supplied with an AC or RF voltage, and wherein at least some of the electrodes are housed in a vacuum chamber maintained in use at a pressure within the range 0.1-10 mbar; a second ion trap downstream of the ion mobility spectrometer, the second ion trap comprising a plurality of electrodes having apertures through which ions may be transmitted, at least some of the electrodes being supplied in use with an AC or RF voltage; an axial drift region downstream of the second ion trap; and an orthogonal time of flight mass analyser comprising a pusher and/or puller electrode, orthogonal drift region and detector, the orthogonal time of flight mass analyser being arranged downstream of the axial drift region.

According to an thirteenth aspect of the present invention, there is provided an ion mobility spectrometer for separating ions according to their ion mobility, the ion mobility spectrometer comprising: a plurality of electrodes having apertures wherein a DC voltage gradient is maintained across at least a portion of the ion mobility spectrometer and at least some of the electrodes are connected to an AC or RF voltage supply.

The ion mobility spectrometer preferably extends between two vacuum chambers so that an upstream section comprising a first plurality of electrodes having apertures is arranged in a vacuum chamber and a downstream section comprising a second plurality of electrodes having apertures is arranged in a further vacuum chamber, the vacuum chambers being separated by a differential pumping aperture.

At least some of the electrodes in the upstream section are preferably supplied with an AC or RF voltage having a frequency within the range 0.1-3.0 MHz. A frequency of 0.5-1.1 MHz is preferred and a frequency of 780 kHz is particularly preferred. The upstream section is preferably arranged to be maintained at a pressure within the range 0.1-10 mbar, preferably approximately 1 mbar.

At least some of the electrodes in the downstream section are preferably supplied with an AC or RF voltage having a frequency within the range 0.1-3.0 MHz. A frequency of 1.8-2.4 MHz is preferred and a frequency of 2.1 MHz is particularly preferred. The downstream section is preferably arranged to be maintained at a pressure within the range $10^{-3}$-$10^{-2}$ mbar.

The voltages applied to the electrodes in the upstream section may be such that a first DC voltage gradient is maintained in use across at least a portion of the upstream section and a second different DC voltage gradient may be maintained in use across at least a portion of the downstream section, the first DC voltage gradient being preferably greater than the second DC voltage gradient. Either voltage gradient does not necessarily have to be linear and indeed a stepped voltage gradient is particularly preferred.

Preferably, the ion mobility spectrometer comprises at least 10, 20, 30, 40, 50, 60, 70, 80, 90 or 100 electrodes. Preferably, at least 60%, 65%, 70%, 75%, 80%, 85%, 90%, 95% of the electrodes forming the ion mobility spectrometer have apertures which are of substantially the same size or area.

Other embodiments are contemplated wherein the second device comprises either a 2D ion trap (e.g. a rod set with front and/or rear trapping electrodes) or a 3D ion trap (e.g. a central ring electrode with front and rear endcap electrodes).

BRIEF DESCRIPTION OF THE DRAWINGS

Various embodiments of the present invention will now be described, by way of example only, and with reference to the accompanying drawings in which:

FIG. 2(*a*) shows a conventional mass spectrum obtained with normal detector gain;

FIG. 2(*b*) shows a comparable conventional mass spectrum obtained by lowering the detector gain;

FIG. 3(*b*) shows an experimentally determined relationship between the mass to charge ratio of a sample of ions and their drift time through an ion mobility spectrometer;

FIG. 7(*a*) illustrates a preferred embodiment of an ion trap, ion gate and ion mobility spectrometer;

FIG. 7(*b*) illustrates the various DC voltages which may be applied to the ion trap, ion gate and ion mobility spectrometer;

FIG. 7(*c*) illustrates how the DC voltage applied to the ion gate may vary as a function of time;

FIG. 7(*d*) illustrates how a quadrupole mass filter may be scanned according to a preferred embodiment;

FIG. 11(*b*) shows a comparable mass spectrum obtained according to a preferred embodiment of the present invention;

FIG. 12(*a*) shows another conventional mass spectrum; and

FIG. 12(*b*) shows a comparable mass spectrum obtained according to a preferred embodiment of the present invention.

DETAILED DESCRIPTION OF THE PREFERRED EMBODIMENTS

Figure 1:
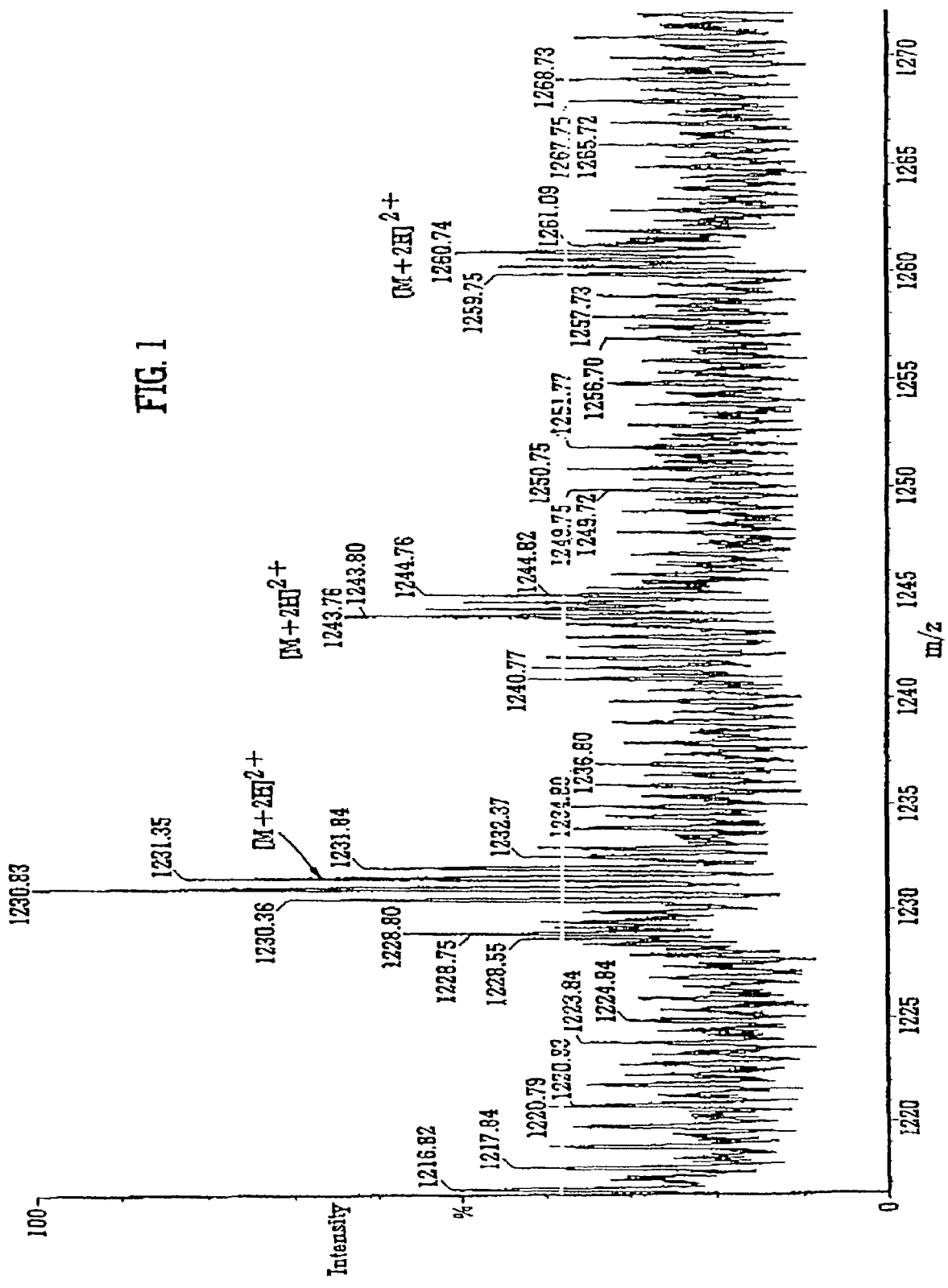
FIG. 1 shows a conventional mass spectrum.
Figure 3A:
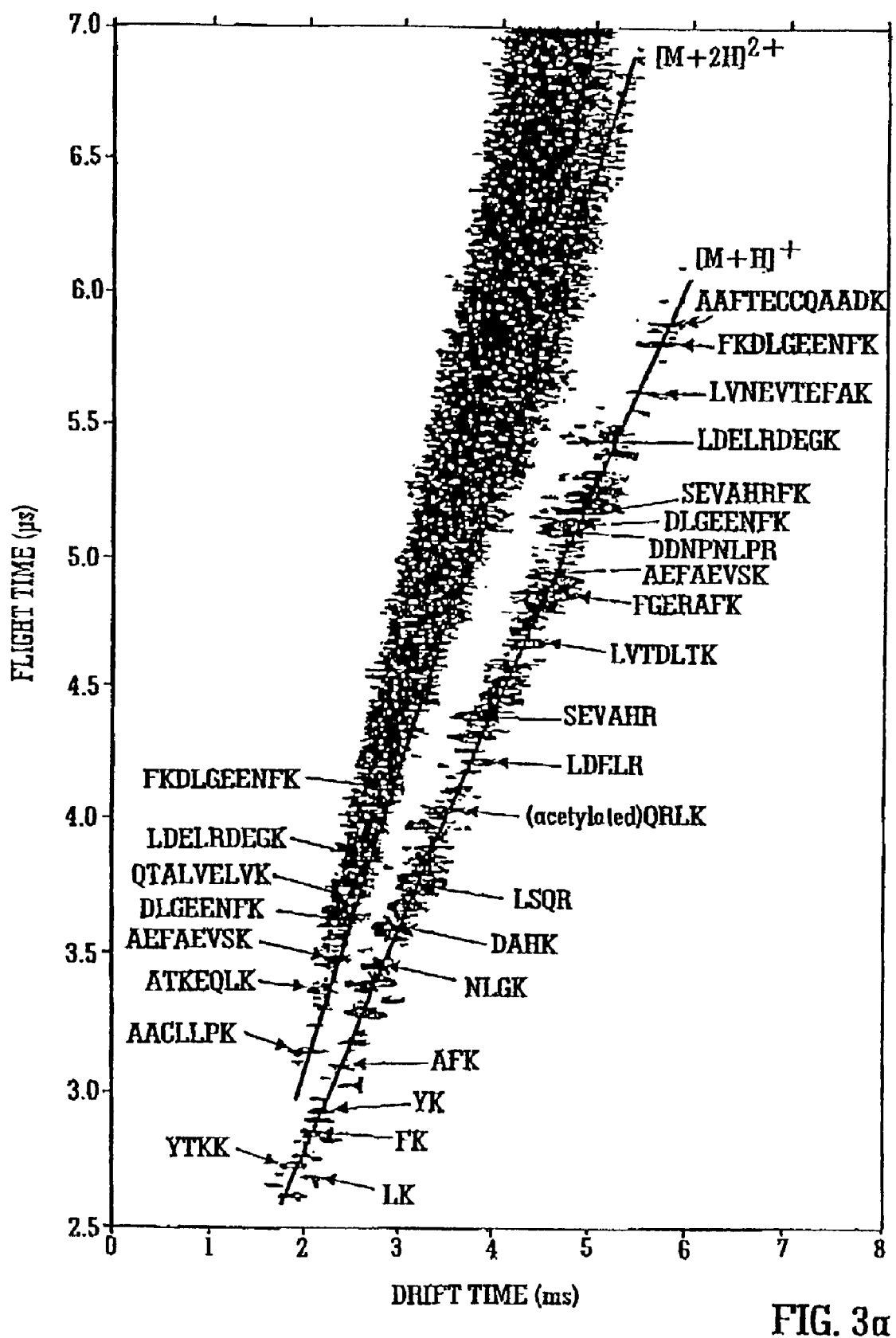
FIG. 3(*a*) shows the known relationship between flight time in a time of flight mass analyser drift region versus drift time in an ion mobility spectrometer for various singly and doubly charged ions.
Figure 3B:
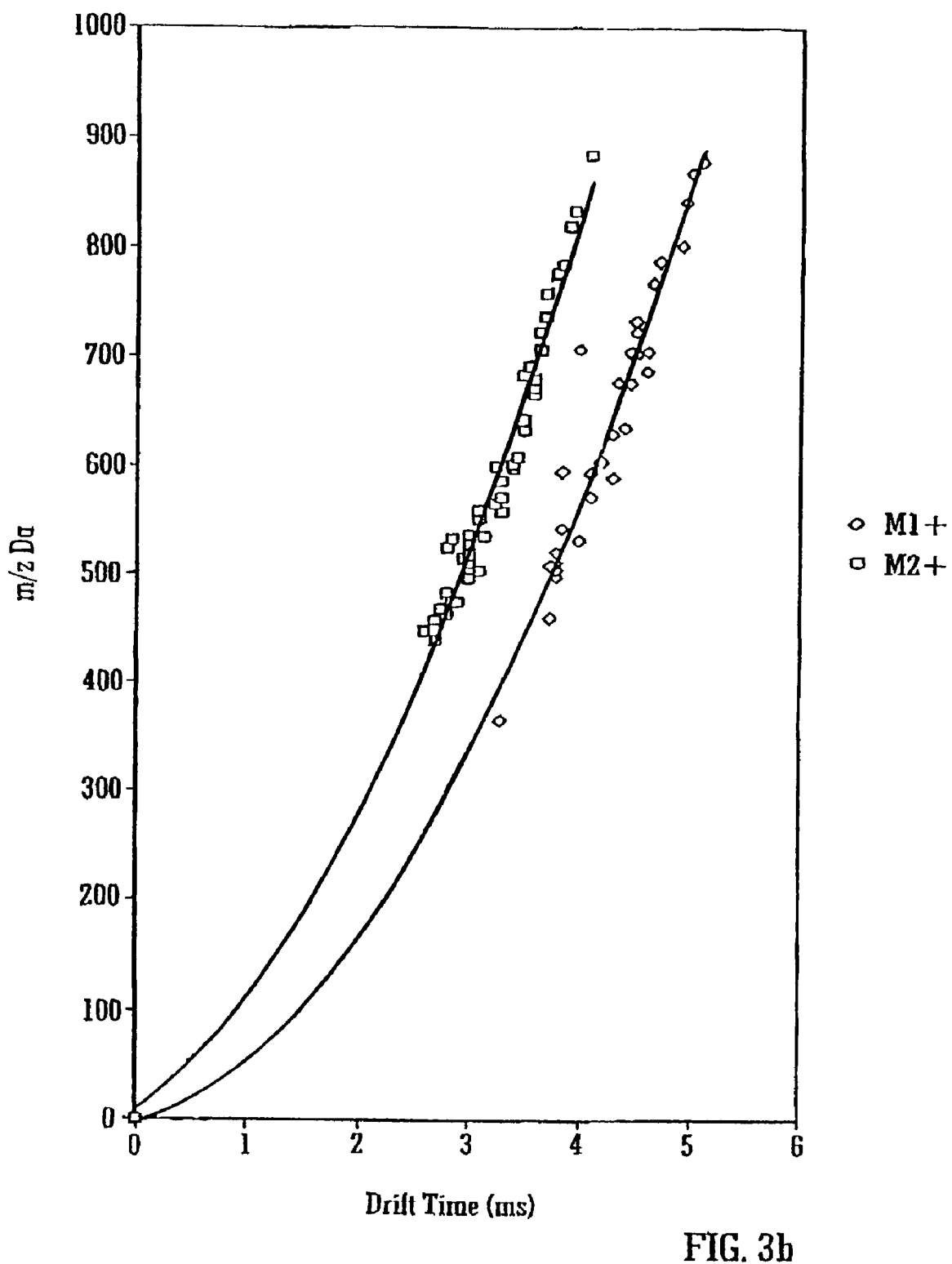

Various embodiments of the present invention will now be described. FIG. 3(*a*) shows the known relationship of flight time in a drift region of a time of flight mass analyser versus drift time in an ion mobility spectrometer for various singly and doubly charged ions. An experimentally determined relationship between the mass to charge ratio of ions and their drift time through an ion mobility spectrometer is shown in FIG. 3(*b*). This relationship can be represented by an empirically derived polynomial expression. As can be seen from these figures, a doubly charged ion having the same mass to charge ratio as a singly charged ion will take less time to drift through an ion mobility spectrometer compared with a singly charged ion. Although the ordinate axis of FIG. 3(*a*) is given as the flight time through the drift region of a time of flight mass analyser, it will be appreciated that this correlates directly with the mass to charge ratio of the ion.

The present inventors have recognised that if a mass filter is provided in combination with an ion mobility spectrometer, and if the mass filter is scanned (i.e. the transmitted range of mass to charge ratios is varied) in synchronisation with the drift of ions through the ion mobility spectrometer, then it is possible to arrange that only ions having a particular charge state (e.g. multiply charged ions) will be transmitted onwardly e.g. to a mass analyser. The ability to be able to substantially filter out singly charged background ions and/or to select ions of one or more specific charge states for analysis represents a significant advance in the art.

Figure 4:
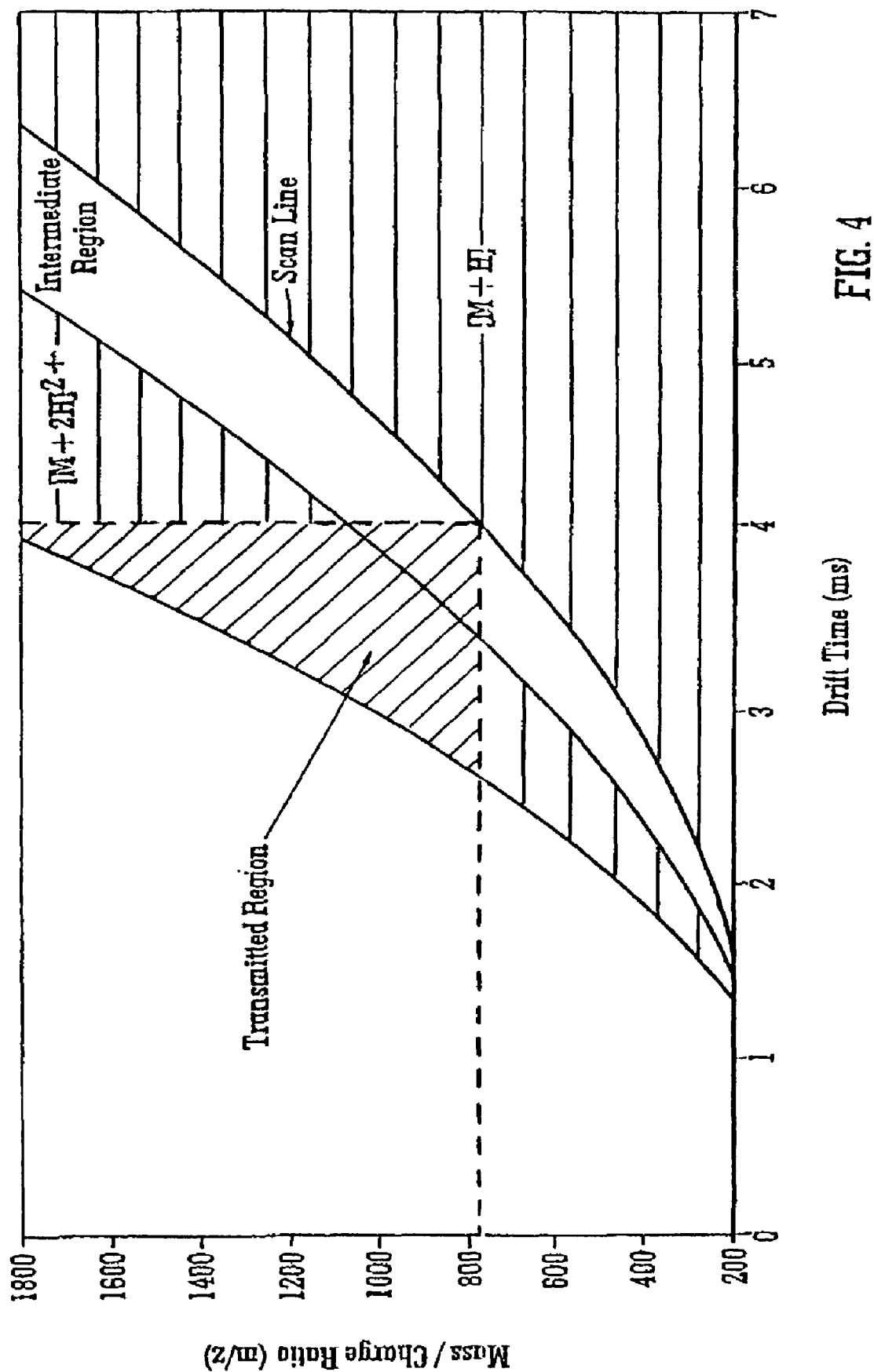
FIG. 4 illustrates the general principle of filtering out singly charged ions according to a preferred embodiment of the present invention.

FIG. 4 illustrates an embodiment of the present invention. The known data of FIG. 3(*a*) and the experimentally derived data of FIG. 3(*b*) can be interpreted such that all ions having the same charge state can be considered to fall within a distinct region or band of a 2D plot of mass to charge ratio versus drift time through an ion mobility spectrometer. In FIG. 4 singly and doubly charged ions are shown as falling within distinct bands with an intermediate region therebetween where very few ions of interest are to be found. Triply and quadruply charged ions etc. are not shown for ease of illustration only. The large area below the "scan line" can be considered to represent singly charged ions and the other area can be considered to represent doubly charged ions.

According to a preferred embodiment, a mass filter is provided which is synchronised with the operation of an ion mobility spectrometer. Considering FIG. 4, it can be seen that at a time around 4 ms after ions have first entered or been admitted to the drift region of the ion mobility spectrometer, ions may be emerging from the ion mobility spectrometer with various different mass to charge ratios. Those ions which emerge with a mass to charge ratio of approximately 1-790 are most likely to be singly charged ions whereas those ions emerging with a mass to charge ratio of approximately 1070-1800 are most likely to be doubly charged ions. Very few, if any, ions will emerge at that point of time with a mass to charge ratio between 790-1070 (which corresponds with the intermediate region of the graph). Therefore, if the mass filter is set at this particular point in time so as to transmit only ions having a mass to charge ratio>790 then it can be assumed that the majority of the singly charged ions will not be onwardly transmitted whereas doubly charged ions (and ions having a higher charge state) will be substantially onwardly transmitted. If the mass filter is operated as a high pass mass filter and if the minimum cut-off mass to charge ratio of the mass filter follows in real time the "scan line" shown in FIG. 4 (i.e. if it tracks the upper predetermined mass to charge ratio for singly charged ions as a function of time) then it will be appreciated that only multiply charged ions will substantially be onwardly transmitted.

According to other embodiments the mass filter may track the lower predetermined mass to charge ratio for doubly charged ions. The cut-off mass to charge ratio may also lie for at least a portion of a cycle within the intermediate region which separates the regions comprising singly and doubly charged ions. The minimum cut-off mass to charge ratio of the mass filter may also vary in a predetermined or random manner between the upper threshold of the singly charged ion region, the intermediate region and the lower threshold of the doubly charged ion region. It will also be appreciated that according to less preferred embodiments, the minimum cutoff mass to charge ratio may fall for at least a portion of time within the region considered to comprise either singly or doubly charged ions. In such circumstances, ions of a potentially unwanted charge state may still be transmitted, but the intensity of such ions will nonetheless be reduced.

According to a preferred embodiment the minimum cut-off mass to charge ratio is varied smoothly, and is preferably increased with time. Alternatively, the minimum cut-off mass to charge ratio may be increased in a stepped manner.

Figure 5:
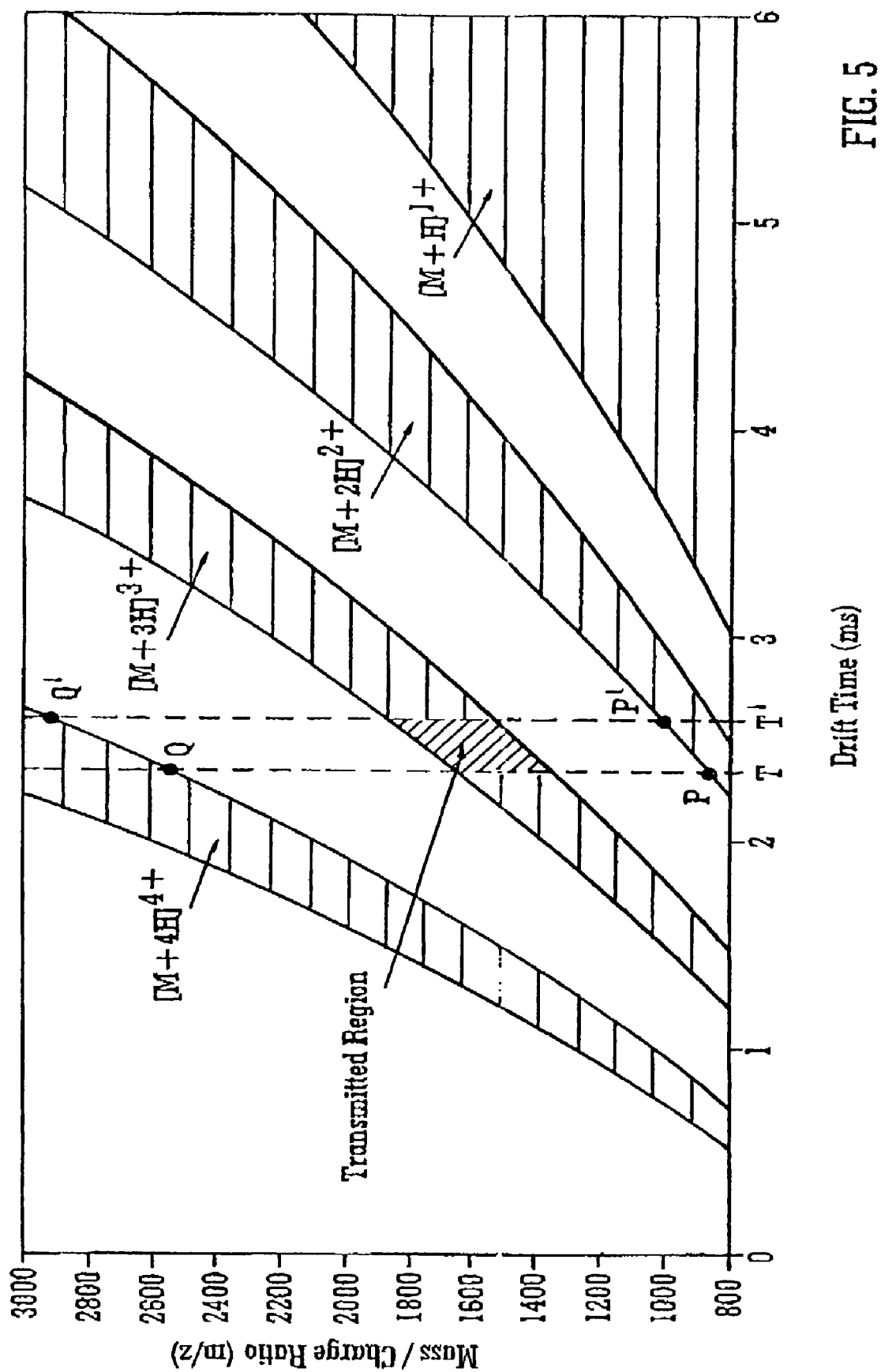
FIG. 5 illustrates the general principle of selecting ions having a specific charge state according to a preferred embodiment of the present invention.

FIG. 5 illustrates how the basic embodiment described in relation to FIG. 4 may be extended so that ions of a specific charge state(s) may be selected. In the embodiment illustrated in FIG. 5 the mass filter is operated as a band pass mass to charge ratio filter so as to select ions of a specific charge state (in this case triply charged ions) in preference to ions having any other charge state. At a time T after ions have first been admitted or introduced into the ion mobility spectrometer, the mass filter, being operated in a band pass mode, is set so as to transmit ions having a mass to charge ratio>P and <Q, wherein P preferably lies on the upper threshold of the region containing doubly charged ions and Q preferably lies on the lower threshold of the region containing quadruply charged ions. The upper and lower mass cut-offs P,Q are preferably smoothly increased with time so that at a later time T', the lower mass to charge ratio cut-off of the band pass mass to charge ratio filter has been increased from P to P' and the upper mass to charge ratio cut-off of the band pass mass to charge ratio filter has been increased from Q to Q'. As with the embodiment described in relation to FIG. 4, the upper and lower mass to charge ratio cut-offs do not need to follow the lower and upper thresholds of any particular charge state region, and according to the other embodiments the upper and lower cut-offs may fall within one or more intermediate regions and/or one or more of the bands in which ions having a particular charge state are to be found. For example, in one embodiment, the lower and upper mass to charge ratio cut-offs may simply follow the thresholds of the region comprising doubly, triply, quadruply etc. charged ions. According to other embodiments two, three, four or more charge states may be selected in preference to any other charge state (e.g. doubly and triply charged ions may be transmitted). Embodiments are also contemplated wherein non-neighbouring charge states (e.g. doubly and quadruply charged ions) are transmitted but not any other charge states.

Figure 6:
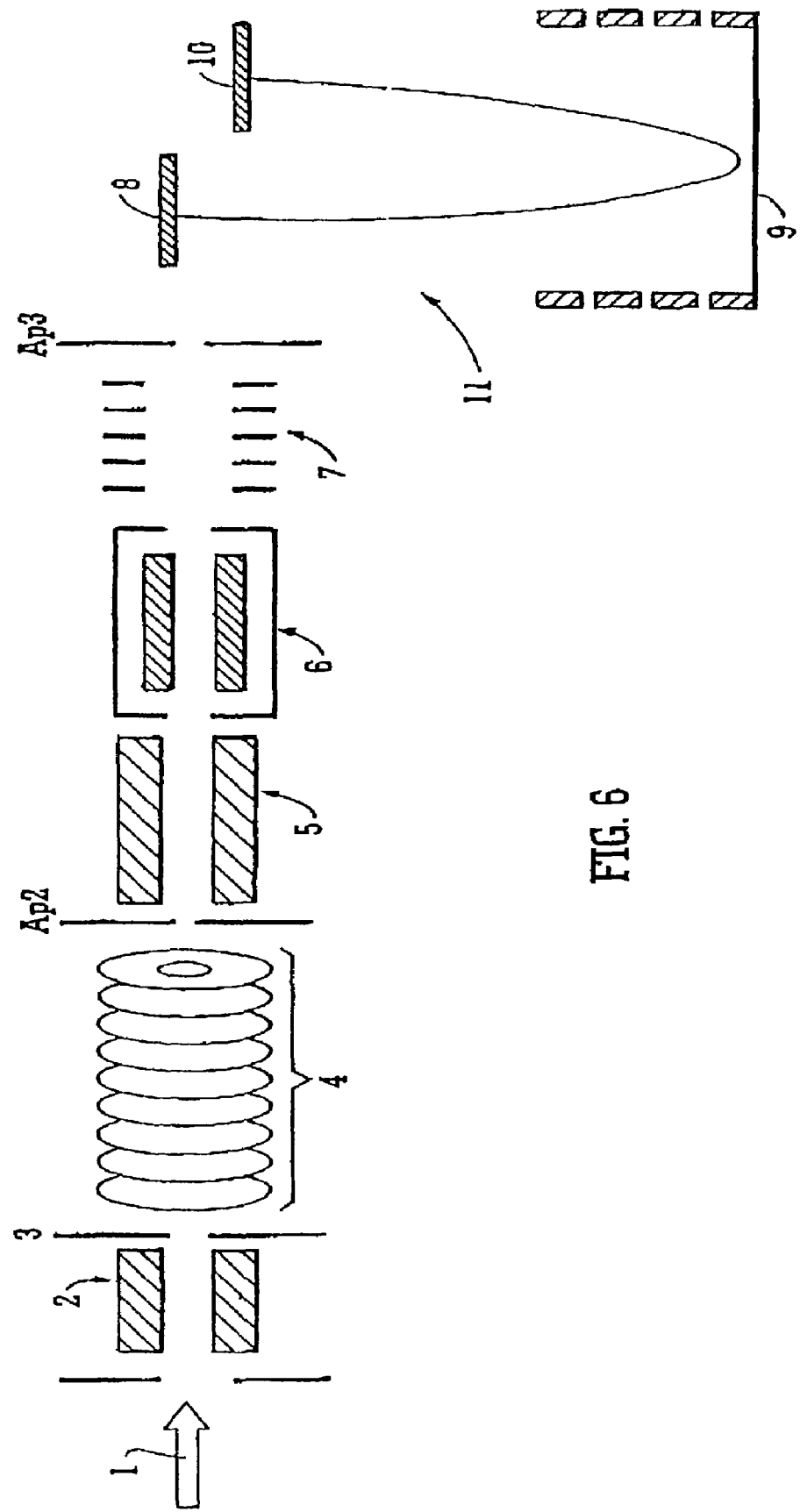
FIG. 6 shows a first main preferred embodiment of the present invention.

FIG. 6 shows a first main preferred embodiment of the present invention. An ion mobility spectrometer 4 is provided. A pulse of ions is admitted to the ion mobility spectrometer 4. A continuous ion source, e.g. Electrospray ion source, preferably generates a beam of ions 1 which are trapped in an ion trap 2 upstream of the ion mobility spectrometer 4 and are then pulsed out of the ion trap 2 by the application of an extraction voltage to an ion gate 3 at the exit of the ion trap 2.

The ion trap 2 may comprise a quadrupole rod set having a length of approximately 75 mm. However, according to a more preferred embodiment the ion trap may comprise an ion tunnel comprising a plurality of electrodes having apertures therein. The apertures are preferably all the same size. In other embodiments at least 60%, 65%, 70%, 75%, 80%, 85%, 90% or 95% of the electrodes have apertures which are substantially the same size. The ion tunnel may preferably comprise approximately 50 electrodes. Adjacent electrodes are preferably connected to opposite phases of an AC or RF voltage supply so that ions are radially confined in use within the ion tunnel.

The voltage applied to the ion gate 3 may be dropped for a short period of time thereby causing ions to be ejected from the ion trap 2 in a substantially pulsed manner into the ion mobility spectrometer 4.

In less preferred embodiments, a pulsed ion source such as a Matrix Assisted Laser Desorption Ionisation ("MALDI") ion source or a Laser Desorption Ionisation ion source may be used instead of a continuous ion source. If a pulsed ion source is used, then ion trap 2 and ion gate 3 may be omitted.

The ion mobility spectrometer 4 is a device which causes ions to become temporally separated based upon their ion mobility. A number of different forms of ion mobility spectrometer may be used.

In one embodiment, the ion mobility spectrometer 4 may comprise a conventional ion mobility spectrometer consisting of a drift tube having a number of guard rings distributed within the drift tube. The guard rings may be interconnected by equivalent valued resistors and connected to a DC voltage source. A linear DC voltage gradient is generated along the length of the drift tube. The guard rings are not connected to an AC or RF voltage source.

According to a particularly preferred embodiment, a new form of ion mobility spectrometer 4 is preferably provided. According to this embodiment the ion mobility spectrometer 4 comprises a number of ring/annular or plate electrodes, or more generally electrodes having an aperture therein through which ions are transmitted. The apertures are preferably all the same size and are preferably circular. In other embodiments at least 60%, 65%, 70%, 75%, 80%, 85%, 90% or 95% of the electrodes have apertures which are substantially the same size or area. A schematic example of the new form of ion mobility spectrometer 4 is shown in FIG. 7(a). The ion mobility spectrometer 4 may comprise a plurality of electrodes 4a, 4b which are either arranged in a single vacuum chamber, or, as shown in FIG. 7(a), are arranged in two adjacent vacuum chambers separated by a differential pumping aperture Ap1. In one embodiment, the portion of the ion mobility spectrometer 4a in an upstream vacuum chamber may have a length of approximately 100 mm, and the portion of the ion mobility spectrometer 4b in a downstream vacuum chamber may have a length of approximately 85 mm. The ion trap 2, ion gate 3 and upstream portion 4a of the ion mobility spectrometer 4 are all preferably provided in the same vacuum chamber which is preferably maintained, in use, at a pressure within the range 0.1-10 mbar. According to less preferred embodiments, the vacuum chamber housing the upstream portion 4a may be maintained at a pressure greater than 10 mbar up to a pressure at or near atmospheric pressure. Also, according to less preferred embodiments, the vacuum chamber may alternatively be maintained at a pressure below 0.1 mbar.

In the preferred embodiment the electrodes comprising the ion trap 2 are maintained at a DC voltage $V_{rf1}$. Ion gate 3 is normally held at a higher DC voltage $V_{trap}$ than $V_{rf1}$, but the voltage applied to the ion gate 3 is periodically dropped to a voltage $V_{extract}$ which is preferably lower than $V_{rf1}$ thereby causing ions to be accelerated out of the ion trap 2 and to be admitted into the ion mobility spectrometer 4.

Adjacent electrodes which form part of the ion trap 2 are preferably connected to opposite phases of a first AC or RF voltage supply. The first AC or RF voltage supply preferably has a frequency within the range 0.1-3.0 MHz, preferably 0.5-1.1 MHz, further preferably 780 kHz.

Alternate electrodes forming the upstream section 4a of the ion mobility spectrometer 4 are preferably capacitively coupled to opposite phases of the first AC or RF voltage supply.

The electrodes comprising the ion trap 2, the electrodes comprising the upstream portion 4a of the ion mobility spectrometer 4 and the differential pumping aperture Ap1 separating the upstream portion 4a from the downstream portion 4b of the ion mobility spectrometer 4 are preferably interconnected via resistors to a DC voltage supply which in one embodiment comprises a 400 V supply. The resistors interconnecting electrodes forming the upstream portion 4a of the ion mobility spectrometer 4 may be substantially equal in value in which case an axial DC voltage gradient is obtained as shown in FIG. 7(b). The DC voltage gradient is shown for ease of illustration as being linear, but may preferably be stepped. The applied AC or RF voltage is superimposed upon the DC voltage and serves to radially confine ions within the ion mobility spectrometer 4. The DC voltage $V_{trap}$ or $V_{extract}$ applied to the ion gate 3 preferably floats on the DC voltage supply. The first AC or RF voltage supply is preferably isolated from the DC voltage supply by a capacitor.

In a similar manner, alternate electrodes forming the downstream portion 4b of the ion mobility spectrometer 4 are preferably capacitively coupled to opposite phases of a second AC or RF voltage supply. The second AC or RF voltage supply preferably has a frequency in the range 0.1-3.0 MHz, preferably 1.8-2.4 MHz, further preferably 2.1 MHz. In a similar manner to the upstream portion 4a, a substantially linear or stepped axial DC voltage gradient is maintained along the length of the downstream portion 4b of the ion mobility spectrometer 4. As with the upstream portion 4a, the applied AC or RF voltage is superimposed upon the DC voltage and serves to radially confine ions within the ion mobility spectrometer 4. The DC voltage gradient maintained across the upstream portion 4a is preferably not the same as the DC voltage gradient maintained across the downstream portion 4b. According to a preferred embodiment, the DC voltage gradient maintained across the upstream portion 4a is greater than the DC voltage gradient maintained across the downstream portion 4b.

The pressure in the vacuum chamber housing the downstream portion 4b is preferably in the range $10^{-3}$ to $10^{-2}$ mbar. According to less preferred embodiments, the pressure may be above $10^{-2}$ mbar, and could be similar in pressure to the pressure of the vacuum chamber housing the upstream portion 4a. It is believed that the greatest temporal separation of ions occurs in the upstream portion 4a due to the higher background gas pressure. If the pressure is too low then the ions will not make enough collisions with gas molecules for a noticeable temporal separation of the ions to occur.

The size of the orifice in the ion gate 3 is preferably of a similar size or is substantially the same internal diameter or size as the differential pumping aperture Ap1. Downstream of the ion mobility spectrometer 4 another differential pumping aperture Ap2 may be provided leading to a vacuum chamber housing a quadrupole mass filter 5. Pre- and post-filters 14a, 14b may be provided. The apertures of the electrodes forming the ion mobility spectrometer 4 are preferably all the same size. In other embodiments at least 60%, 65%, 70%, 75%, 80%, 85%, 90% or 95% of the electrodes have apertures which are substantially the same size.

In another preferred embodiment of the present invention the ion mobility spectrometer 4 may comprise an ion tunnel comprised of a plurality of segments. In one embodiment 15 segments may be provided. Each segment may comprise two electrodes having apertures interleaved with another two electrodes having apertures. All four electrodes in a segment are preferably maintained at the same DC voltage but adjacent electrodes are connected to opposite phases of the AC or RF supply. The DC and AC/RF voltage supplies are isolated from one another. Preferably, at least 90% of all the electrodes forming the ion tunnel comprised of multiple segments have apertures which are substantially similar or the same in size.

Typical drift times through the ion mobility spectrometer 4 are of the order of a few ms. After all the generated ions have traversed the ion mobility spectrometer 4 a new pulse of ions may be admitted which marks the start of a new cycle of operation. Many cycles may be performed in a single experimental run.

An important feature of the preferred embodiment is the provision of a mass filter which is varied in a specified manner in conjunction with the operation of the ion mobility spectrometer 4. In the first main preferred embodiment a quadrupole rod set mass filter 5 is used.

If the mass filter 5 is synchronised to the start of the pulse of ions being admitted into the ion mobility spectrometer 4, then the mass filter 5 can be set to transmit (in conjunction with the operation of the ion mobility spectrometer 5) only those ions having a mass to charge ratio that corresponds at any particular point in time with the charge state of the ions of interest. Preferably, the mass filter should be able to sweep the chosen mass to charge ratio range on at least the time scale of ions drifting through the drift region. In other words, the mass filter should be able to be scanned across the desired mass to charge ratio range in a few milliseconds. Quadrupole mass filters 5 are capable of operating at this speed.

According to the first main preferred embodiment, either the AC (or RF) voltage and/or the DC voltage applied to the quadrupole mass filter 5 may be swept in synchronisation with the pulsing of ions into the ion mobility spectrometer 4. As discussed above in relation to FIGS. 4 and 5, the quadrupole mass filter 5 may be operated in either a high pass or band pass mode depending on whether e.g. multiply charged ions are preferred in general, or whether ions having a specific charge state are preferred. The varying of a mass filtering characteristic of the quadrupole mass filter 5 is such that ions having a favoured charge state (or states) are preferably onwardly transmitted, preferably to the at least near exclusion of other charge states, for at least part of the cycle time Tm between pulses of ions being injected into the ion mobility spectrometer 4. FIGS. 7(c) and (d) show the inter-relationship between ions being pulsed out of the ion trap 2 into the ion mobility spectrometer 4, and the scanning of the mass filter 5. Synchronisation of the operation of the mass filter 5 with the drift times of desired ions species through the ion mobility spectrometer 4 enables a duty cycle of ~100% to be obtained for ions having the charge state(s) of interest.

Referring back to FIG. 6, a collision (or gas) cell 6 may be provided preferably downstream of the ion mobility spectrometer 4 and preferably downstream of the quadrupole mass filter 5. Ions may be arranged so that they are sufficiently energetic when they enter the collision cell 6 so that they collide with gas molecules present in the gas cell 6 and fragment into daughter ions. Subsequent mass analysis of the daughter ions yields valuable mass spectral information about the parent ion(s). Ions may also be arranged so that they enter the gas or collision cell 6 with much less energy, in which case they may not substantially fragment. The energy of ions entering the collision cell 6 can be controlled e.g. by setting the level of a voltage gradient experienced by the ions prior to entering the collision cell 6. Since the voltage gradient can be switched near instantaneously, the collision cell 6 can, in effect, be considered to be switchable between a relatively high fragmentation mode and a relatively low fragmentation mode.

Ion optical lenses 7 are preferably provided downstream of the collision cell 6 to guide ions through a further differential pumping aperture Ap3 and into an analyser chamber containing a mass analyser. According to a particularly preferred embodiment, the mass analyser comprises an orthogonal acceleration time of flight mass analyser 11 having a pusher and/or puller electrode 8 for injecting ions into an orthogonal drift region. A reflectron 9 is preferably provided for reflecting ions travelling through the orthogonal drift region back towards a detector 10. As is well known in the art, at least some of the ions in a packet of ions entering an orthogonal acceleration time of flight mass analyser will be orthogonally accelerated into the orthogonal drift region. Ions will become temporally separated in the orthogonal drift region in a manner dependent upon their mass to charge ratio. Ions having a lower mass to charge ratio will travel faster in the drift region and will reach the detector 10 prior to ions having a higher mass to charge ratio. The time it takes an ion to drift through the drift region and to reach the detector 10 can be used to accurately determine the mass to charge ratio of the ion in question. The intensity of ions and their mass to charge ratios can be used to produce a mass spectrum.

Figure 8:
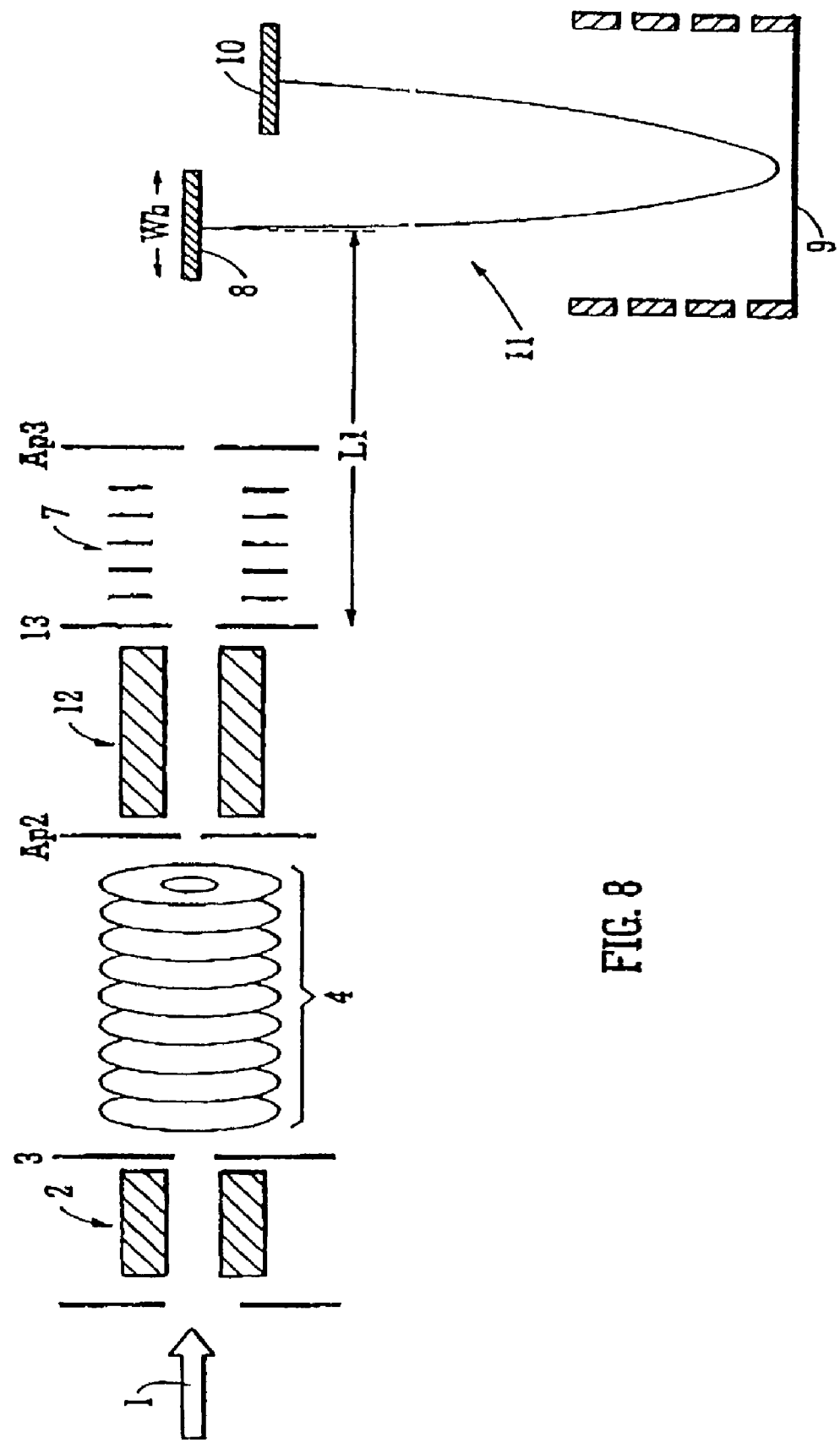
FIG. 8 shows a second main preferred embodiment of the present invention.

FIG. 8 shows a second main preferred embodiment of the present invention. The ion mobility spectrometer 4, optional ion trap 2 and ion gate 3 may take any of the forms described in relation to the first main preferred embodiment of the present invention. Similarly, the ion sources described in relation to the first main preferred embodiment may also be used in relation to the second main preferred embodiment.

The second main preferred embodiment differs primarily from the first main preferred embodiment in that the quadrupole mass filter 5 is replaced with a different form of mass filter, namely an axial time of flight or drift region having a length L1 and an injection electrode 8. Ions are preferably pulsed into the axial time of flight region and the injection electrode 8 is operated in conjunction with the pulsing of ions into the axial time of flight region so that only ions having a specific mass to charge ratio are injected by the injection electrode 8 and hence onwardly transmitted to e.g. the detector 10. The injection electrode 8 preferably comprises the pusher and/or puller electrode 8 of an orthogonal acceleration time of flight mass analyser 11.

In order to pulse ions into the axial time of flight region, a second ion trap 12 and optionally a second ion gate 13 are preferably provided. Ions received from the ion mobility spectrometer 4 are trapped in the second ion trap 12. Packets of ions are then preferably periodically released from the second ion trap 12, for example, by lowering the DC voltage applied to the second ion gate 13 in a similar manner to the way ions may be released from the first ion gate 3. In other embodiments, however, the second ion trap 12 may trap and release ions without requiring a distinct second ion gate 13.

The second ion trap 12 preferably comprises an ion tunnel ion trap comprising a plurality of electrodes having apertures therein. The electrodes may take the form of rings or other annular shape or rectangular plates. As with the ion mobility spectrometer 4, preferably at least 60%, 65%, 70%, 80%, 85%, 90% or 95% of the electrodes forming the ion tunnel ion trap have apertures which are substantially the same size or area. Adjacent electrodes are preferably connected to opposite phases of an AC or RF voltage supply so that ions are radially confined within the second ion trap 12. A particular advantage of an ion tunnel ion trap is that the DC voltage supplied to each electrode can be individually controlled. This enables numerous different axial DC voltage profiles to be created along the length of the ion tunnel ion trap 12. A particularly preferred embodiment is to provide, in one mode of operation, a V-shaped DC potential profile comprising an upstream portion having a negative DC voltage gradient and a downstream portion having a positive DC voltage gradient so that (positive) ions become trapped towards the centre of the ion trap 12. If the positive DC voltage gradient maintained across the downstream portion of the ion trap 12 is then changed to a zero gradient or more preferably to a negative gradient, then (positively charged) ions will be accelerated out the ion trap 12 as a pulse of ions. In this particular embodiment a distinct second ion gate 13 may then become redundant.

According to other embodiments, the second ion trap 12 may comprise a 3D-quadrupole ion trap comprising a central doughnut shaped electrode together with two endcap electrodes. According to another embodiment, the second ion trap 12 may comprise a hexapole ion guide. However, this embodiment is less preferred since no axial DC voltage gradient is present to urge ions out of the hexapole ion guide. It is for this reason that an ion tunnel ion trap is particularly preferred.

The drift region L1 between the second ion gate 13 (or exit of the second ion trap 12) and the centre of the pusher/puller electrode 8 is such that the ions in a packet of ions released from the second ion trap 12 will become temporally dispersed by the time that they arrive at the pusher electrode 8. Ions having a smaller mass to charge ratio will reach the pusher/puller electrode 8 before ions having a larger mass to charge ratio. The pusher/puller electrode 8 can be set so as to inject ions into the orthogonal acceleration time of flight mass analyser 11 at a predetermined time after they were first released from the second ion trap 12. Since the time of arrival of an ion at the pusher/puller electrode 8 is dependent upon its mass to charge ratio, it can be arranged that only ions having a certain mass to charge ratio will be injected by the pusher/puller electrode 8 into the orthogonal drift region of the orthogonal acceleration time of flight mass analyser 11 by appropriate setting of the time delay.

Figure 9:
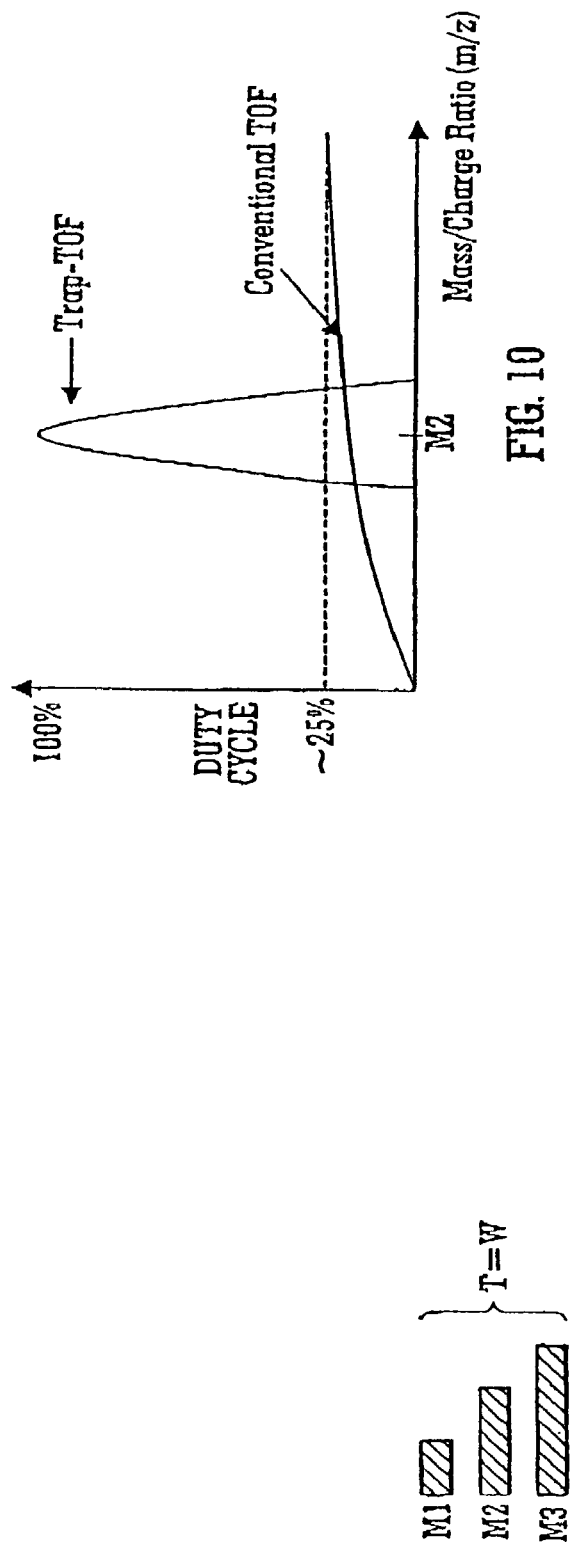
FIG. 9 shows how ions of differing mass to charge ratios become temporally separated in an axial drift region.

FIG. 9 illustrates how the axial time of flight region in combination with the pusher electrode 8 may act as a mass filter. L1 is the distance from the exit of the second ion trap 12 or second ion gate 13 to the centre of the pusher electrode 8. Wb is the width of the pusher electrode. At a time T=0, ions are released for a period W from the exit of the second ion trap 12. After a period of time Td ions of mass to charge ratio M2 have reached the pusher/puller electrode 8 and the pusher/puller electrode 8 is preferably energised so that ions of a mass to charge ratio M2 are injected into the orthogonal drift region of the time of flight mass analyser 11. This results in a duty cycle of ~100% for ions of mass to charge ratio M2. Ions having a mass to charge ratio M1 which is greater than M2 have not reached the pusher/puller electrode 8 by the time that the pusher/puller electrode 8 is energised, and hence these ions are not injected into the orthogonal acceleration time of flight mass analyser 11. Similarly, ions having a mass to charge ratio M3 which is smaller than M2 have already passed the pusher electrode 8 by the time that the pusher/puller electrode 8 is energised, and hence these ions are also not injected into the orthogonal acceleration time of flight mass analyser 11.

Preferably, after a pulse of ions has been admitted into the axial drift region the pusher electrode 8 is energised after a predetermined time delay Td to inject only certain ions. The predetermined time delay Td is then increased and the process repeated. Embodiments are also contemplated wherein, for example, 4-5 packets of ions are admitted into the axial drift region and the pusher electrode duly energised 4-5 times before the predetermined time delay Td is increased. For sake of illustration only, if a single pulse of ions is released from the second ion trap 12 and the pulse takes a maximum of ~100μs to drift through the axial drift region, then the delay time Td may be increased approximately every 100μs. If a cycle is taken to be about 5 ms (i.e. the maximum time for an ion to drift through the ion mobility spectrometer 4), then the predetermined delay time Td may be increased approximately 50 times per cycle.

Figure 10:
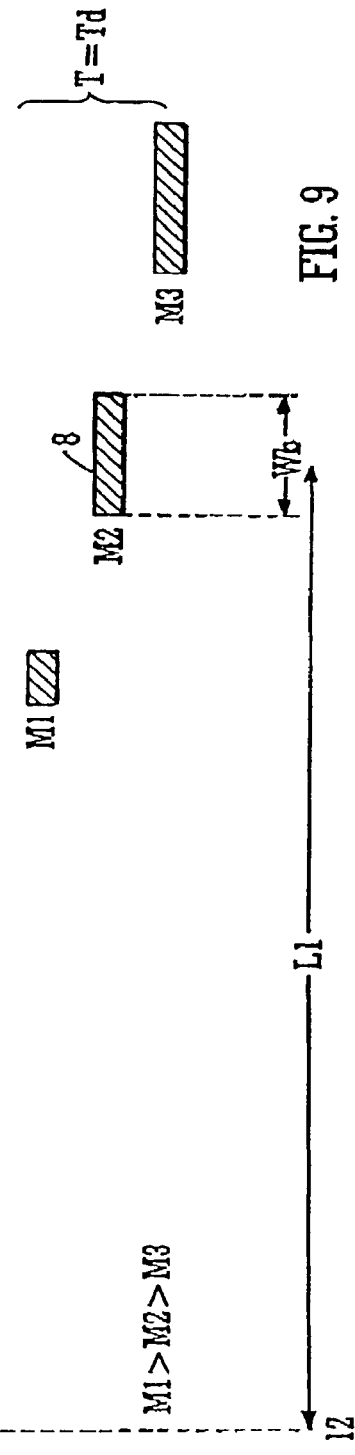
FIG. 10 illustrates how the duty cycle of an ion trap-time of flight mass analyser increases to ~100% for a relatively narrow mass to charge ratio range compared with a typical maximum duty cycle of ~25% obtained by operating the time of flight mass analyser in a conventional manner.

By adjusting the length of the extraction pulse W and the predetermined time delay Td it is possible to optimise the transmission for any particular mass to charge ratio (or limited mass to charge ratio range) as desired. The period W may be adjusted such that the size of the packet of ions released from the second ion trap 12 exactly fills the pusher electrode 8 for a particular mass to charge ratio. The improvement in duty cycle for this method over a continuously pulsing orthogonal acceleration time of flight mass analyser is shown in FIG. 10.

As will be appreciated, the second ion trap 12, second ion gate 13, drift region L1 and pusher electrode 8 operate to act as a mass filter with a high duty cycle over a limited mass to charge ratio range.

For ease of illustration only, a collision (or gas) cell 6 is not shown in FIG. 8. However, a separate collision cell 6 as described in relation to the first main preferred embodiment may be provided upstream or downstream of the second ion trap 12. According to a particularly preferred embodiment, the second ion trap 12 may act both as an ion trap and as a collision cell in both main preferred embodiments. The ion tunnel ion trap/collision cell may comprise a plurality of segments (e.g. 15 segments), each segment comprising four electrodes interleaved with another four electrodes. All eight electrodes in a segment are preferably maintained at the same DC voltage, but adjacent electrodes are preferably supplied with opposite phases of an AC or RF voltage supply. A collision gas preferably nitrogen or argon may be supplied to the collision cell at a pressure preferably of $10^{-3}$-$10^{-2}$ mbar. Ions may be trapped and/or fragmented in the ion trap/collision cell by appropriate setting of the DC voltages applied to the electrodes and the energy that ions are arranged to have upon entering the ion trap/collision cell.

Figure 11A:
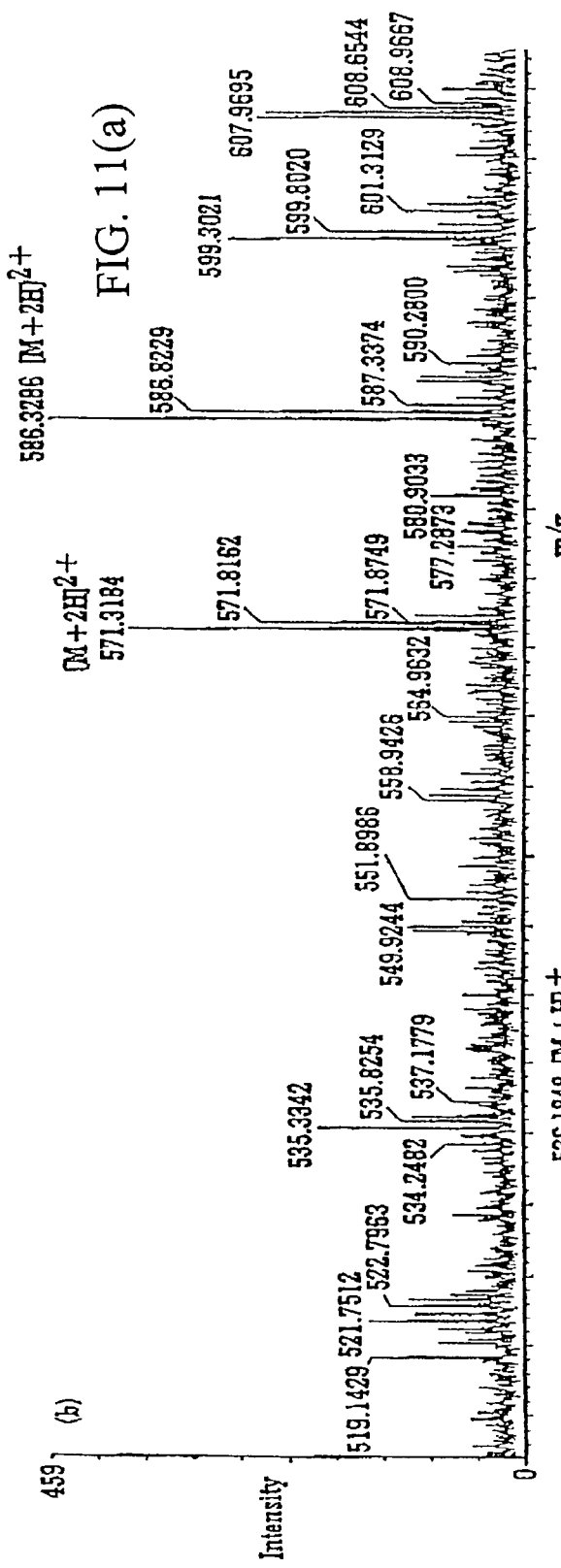
FIG. 11(*a*) shows a conventional mass spectrum.
Figure 11B:
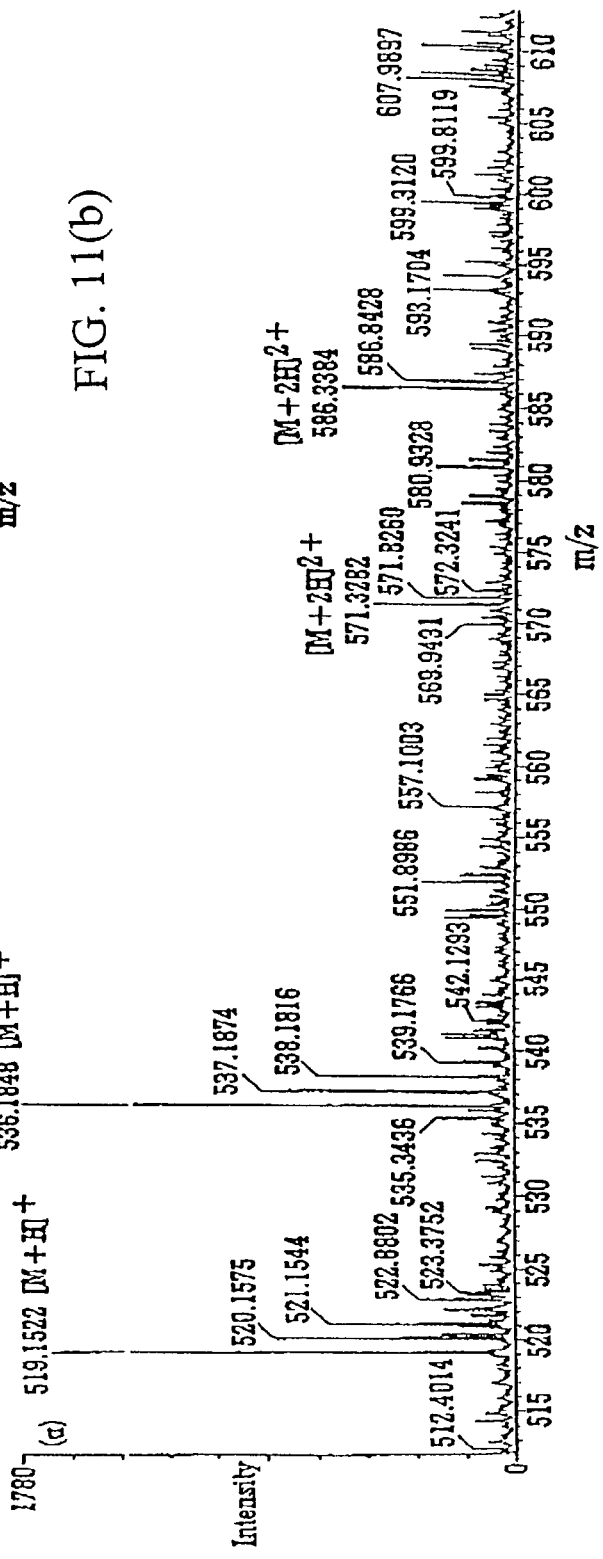

Some experimental results are shown in FIGS. 11(a) and (b). FIG. 11(a) shows a conventional mass spectrum i.e. without any charge state selection being performed. FIG. 11(b) shows a comparable mass spectrum obtained with charge state selection according to the preferred embodiment. As can be seen, singly charged ions are substantially absent from the mass spectrum. Similarly, FIG. 12(a) shows another conventional mass spectrum and FIG. 12(b) shows a comparable mass spectrum obtained with charge state selection according to the preferred embodiment. Again, it can be seen that singly charged ions are substantially absent from the mass spectrum.

In both the first main preferred embodiment and the second main preferred embodiment, the mass filter (e.g. quadrupole 5 or axial time of flight region and injection electrode 8) are shown and described as being downstream of the ion mobility spectrometer 4. However, according to other embodiments the mass filter (e.g. quadrupole 5 or axial time of flight region and injection electrode 8) may be arranged upstream of the ion mobility spectrometer 4.

Furthermore, although the first and second main preferred embodiments have been described in relation to being able to filter out e.g. singly charged ions in preference to multiply charged ions, other embodiments are contemplated wherein singly charged ions are preferentially selected and onwardly transmitted whilst other charge state(s) are attenuated.

Other embodiments are contemplated wherein the AC or RF voltage supplied to electrode(s) in an ion tunnel (either an ion mobility spectrometer and/or ion trap) may be non-sinusoidal and may, for example, take the form of a square wave.

Yet further embodiments are contemplated wherein other types of mass filter are used instead (or in addition to) a quadrupole mass filter or an axial drift region in combination with an injection electrode as described in relation to the two main preferred embodiments. In particular, embodiments are contemplated wherein a RF hexapole, octapole or other multipole rod set mass filter is used. Alternatively, a RF ring set or a RF ion trap (either 2D or 3D) may be used.

According to a preferred embodiment both the upstream ion trap 2 and the ion mobility spectrometer 4 may comprise an ion tunnel i.e. a plurality of electrodes wherein each electrode has an aperture therein through which ions are transmitted. The electrodes, preferably having substantially similar sized apertures, forming each ion tunnel may comprise essentially a square or rectangular plate or a ring. In either case the apertures are preferably circular. According to various embodiments, the ion tunnel ion trap and/or ion mobility spectrometer may comprise at least 10, 20, 30, 40, 50, 60, 70, 80, 90 or 100 electrodes of which at least 60%, 65%, 70%, 75%, 80%, 85%, 90% or 95% have apertures which are substantially the same size or area. As will be appreciated, the construction of an ion tunnel which preferably comprises a large number of plate like electrodes is quite distinct from a multipole rod set ion guide.

Embodiments of the invention are also contemplated wherein the DC voltage profile along the length of the ion mobility spectrometer and/or ion trap and/or collision cell is not strictly linear, but rather has a stepped profile.

Although the present invention has been described with reference to preferred embodiments, it will be understood by those skilled in the art that various changes in form and detail may be made without departing from the scope of the invention as set forth in the accompanying claims.

The invention claimed is:

1. A method of mass spectrometry comprising:
providing a pulse of ions and performing the following steps before providing another pulse of ions:
(a) temporally separating at least some of said ions according to their ion mobility in a first device;
(b) mass filtering at least some of said ions according to their mass to charge ratio in a second device; and
(c) continuously varying a mass filtering characteristic of said second device so that multiply charged ions having a first charge state are onwardly transmitted in preference to singly charged ions.

2. A method as claimed in claim 1, wherein said first charge state is selected from the group consisting of: (i) doubly charged ions; (ii) triply charged ions; (iii) quadruply charged ions; and (iv) ions having five or more charges.

3. A method as claimed in claim 1, wherein said first device comprises an ion mobility spectrometer.

4. A method as claimed in claim 3, wherein said ion mobility spectrometer comprises a plurality of electrodes having apertures wherein a DC voltage gradient is maintained across at least a portion of said ion mobility spectrometer and at least some of said electrodes are connected to an AC or RF voltage supply.

5. A method as claimed in claim 3, wherein said ion mobility spectrometer comprises a drift tube together with one or more electrodes for maintaining an axial DC voltage gradient along at least a portion of said drift tube.

6. A method as claimed in claim 1, wherein said second device comprises a quadrupole rod set mass filter.

7. A method as claimed in claim 6, wherein said quadrupole mass filter is operated as a high pass mass to charge ratio filter so as to substantially only transmit ions having a mass to charge ratio greater than a minimum value.

8. A method as claimed in claim 6, wherein said quadrupole mass filter is operated as a band pass mass to charge ratio filter so as to substantially only transmit ions having a mass to charge ratio greater than a minimum value and smaller than a maximum value.

9. A method as claimed in claims 7, wherein said step of progressively varying a mass filtering characteristic of said second device comprises scanning said quadrupole mass filter so as to progressively increase said minimum value.

10. A method as claimed in claim 9, wherein said quadrupole mass filter is scanned in a substantially continuous manner.

11. A method as claimed in claim 9, wherein said quadruple mass filter is scanned in a substantially stepped manner.

12. A method as claimed in claim 1, wherein said second device comprises a drift region having an axis and an injection electrode for injecting at least some ions in a direction substantially orthogonal to said axis.

13. A method as claimed in claim 12, wherein said injection electrode comprises a pusher and/or puller electrode of an orthogonal acceleration time of flight mass analyser.

14. A method as claimed in claim 12, further comprising an ion trap upstream of said drift region for storing and periodically releasing ions.

15. A method as claimed in claim 14, wherein said injection electrode is arranged to inject ions a predetermined period of time after ions have first been released from said ion trap upstream of said drift region, said period of time being set so that only ions having a mass to charge ratio within a desired range are substantially injected by said injection electrode.

16. A method as claimed in claim 15, wherein packets of ions are repeatedly released from said ion trap and said predetermined time delay is progressively increased.

17. A method as claimed in claim 1, wherein said step of providing a pulse of ions comprises providing a pulsed ion source.

18. A method as claimed in claim 17, wherein said pulsed ion source is selected from the group consisting of: (i) a Matrix Assisted Laser Desorption Ionisation ("MALDI") ion source; and (ii) a Laser Desorption Ionisation ion source.

19. A method as claim in claim 1, wherein said step of providing a pulse of ions comprises providing a continuous ion source and an ion trap for storing ions and periodically releasing ions.

20. A method as claimed in claim 19, wherein said continuous ion source is selected from the group consisting of: (i) an Electrospray ion source; (ii) an Atmospheric Pressure Chemical Ionisation ("APCI") ion source; (iii) an Electron Impact ("EI") ion source; (iv) an Atmospheric Pressure Photon Ionisation ("APPI") ion source; and (v) a Chemical Ionisation ("CI") ion source.

21. A method as claimed in claim 1, further comprising providing a collision cell wherein in one mode of operation at least some ions entering said collision cell are caused to fragment.

22. A method as claimed in claim 1, further comprising providing an orthogonal acceleration time of flight mass analyser.

23. A method of mass spectrometry comprising:
providing a pulse of ions;
separating at least some of said ions according to their ion mobility in an ion mobility spectrometer;
using a mass filter having a variable mass to charge ratio cut-off to mass filter at least some of said ions; and
continuously increasing said mass to charge ratio cut-off in synchronisation with said ion mobility spectrometer.

24. A method of mass spectrometry comprising:
separating at least some ions according to their ion mobility;
mass filtering at least some ions; and
arranging for multiply charged ions to be transmitted and for singly charged ions to be attenuated.

25. A method of reducing unwanted singly charged ions from a mass spectrum, comprising:
separating ions in an ion mobility spectrometer;
passing said ions to a mass filter; and
arranging said mass filter to have a mass to charge ratio cut-off which continuously increases in time, said cut-off being predetermined based upon the known drift times of singly and doubly charged ions through said ion mobility spectrometer.

26. A method of mass spectrometry, comprising:
providing a pulse of ions;
temporally separating at least some of said ions according to their ion mobility in an ion mobility spectrometer;
providing a quadrupole rod set mass filter; and
continuously increasing a mass to charge ratio cut-off of said mass filter so that multiply charged ions are onwardly transmitted in preference to singly charged ions.

27. A method of mass spectrometry, comprising:
providing a pulse of ions;
temporally separating at least some of said ions according to their ion mobility in an ion mobility spectrometer;
providing a drift region and an injection electrode;
repeatedly pulsing ions into said drift region and causing said injection electrode to inject at least some of said ions in a substantially orthogonal direction after a delay time; and
repeatedly varying said delay time so that multiply charged ions are onwardly transmitted in preference to singly charged ions.

28. A method as claimed in claim 1, wherein said second device comprises a 2D ion trap.

29. A method as claimed in claim 1, wherein said second device comprises a 3D ion trap.

30. A mass spectrometer comprising:
a first device for temporally separating ions according to their ion mobility;
a second device for mass filtering at least some of said ions according to their mass to charge ratio; and
a controller which is arranged to continuously vary a mass filtering characteristic of said second device so that multiply charged ions having a first charge state are onwardly transmitted in preference to singly charged ions.

31. A mass spectrometer as claimed in claim 30, wherein said first charge state is selected from the group consisting of: (i) doubly charged ions; (ii) triply charged ions; (iii) quadruply charged ions; and (iv) ions having five or more charges.

32. A mass spectrometer as claimed in claim 30, wherein said first device comprises an ion mobility spectrometer.

33. A mass spectrometer as claimed in claim 32, wherein said ion mobility spectrometer comprises a plurality of electrodes having apertures wherein a DC voltage gradient is maintained across at least a portion of said ion mobility spectrometer and at least some of said electrodes are connected to an AC or RF voltage supply.

34. A mass spectrometer as claimed in claim 32, wherein said ion mobility spectrometer comprises a drift tube together with one or more electrodes for maintaining an axial DC voltage gradient along at least a portion of said drift tube.

35. A mass spectrometer as claimed in claim 30, wherein said second device comprises a quadrupole rod set mass filter.

36. A mass spectrometer as claimed in claim 35, wherein said quadrupole mass filter is operated as a high pass mass to charge ratio filter so as to substantially only transmit ions having a mass to charge ratio greater than a minimum value.

37. A mass spectrometer as claimed in claim 35, wherein said quadrupole mass filter is operated as a band pass mass to charge ratio filter so as to substantially only transmit ions having a mass to charge ratio greater than a minimum value and smaller than a maximum value.

38. A mass spectrometer as claimed in claim 36, wherein said quadrupole mass filter is scanned so that said minimum value is progressively increased.

39. A mass spectrometer as claimed in claim 30, wherein said second device comprises a drift region having an axis and an injection electrode for injecting at least some ions in a direction substantially orthogonal to said axis.

40. A mass spectrometer as claimed in claim 39, wherein said injection electrode comprises a pusher and/or puller electrode of an orthogonal acceleration time of flight mass analyser.

41. A mass spectrometer as claimed in claim 39, further comprising an ion trap upstream of said drift region for storing and periodically releasing ions.

42. A mass spectrometer as claimed in claim 41, wherein said injection electrode is arranged to inject ions a predetermined period of time after ions have been released from said ion trap upstream of said drift region, said period of time being set so that only ions having a mass to charge ratio within a desired range are substantially injected by said injection electrode.

43. A mass spectrometer as claimed in claim 42, wherein packets of ions are repeatedly released from said ion trap and said predetermined time delay is progressively increased.

44. A mass spectrometer as claimed in claim 30, further comprising a pulsed ion source.

45. A mass spectrometer as claimed in claim 44, wherein said pulsed ion source is selected from the group consisting of: (i) a Matrix Assisted Laser Desorption Ionisation ("MALDI") ion source; and (ii) a Laser Desorption Ionisation ion source.

46. A mass spectrometer as claimed in claim 30, further comprising a continuous ion source and an ion trap for storing and periodically releasing ions.

47. A mass spectrometer as claimed in claim 46, wherein said continuous ion source is selected from the group consisting of: (i) an Electrospray ion source; (ii) an Atmospheric Pressure Chemical Ionisation ("APCI") ion source; (iii) an Electron Impact ("EI") ion source; (iv) an Atmospheric Pressure Photon Ionisation ("APPI") ion source; and (v) a Chemical Ionisation ("CI") ion source.

48. A mass spectrometer as claimed in claim 30, further comprising a collision cell wherein in one mode of operation at least some ions entering said collision cell are caused to fragment.

49. A mass spectrometer as claimed in claim 30, further comprising an orthogonal acceleration time of flight mass analyser.

50. A mass spectrometer as claimed in claim 30, wherein said second device comprises a 2D ion trap.

51. A mass spectrometer as claimed in claim 30, wherein said second device comprises a 3D ion trap.

52. A mass spectrometer comprising:
an ion mobility spectrometer;
a quadrupole mass filter; and
control means for continuously increasing the mass to charge ratio cut-off of said quadrupole mass filter in synchronisation with said ion mobility spectrometer.

53. A mass spectrometer comprising:
an ion source;
an ion mobility spectrometer for separating ions according to both their mass and charge state;
a mass filter;
control means for controlling said ion mobility spectrometer and said mass filter; and
a mass analyser;
wherein said control means is arranged to control said ion mobility spectrometer and said mass filter to attenuate multiply charged ions so that there is a higher proportion of singly charged ions to multiply charged ions downstream of said ion mobility spectrometer and said mass filter compared with upstream of said ion mobility spectrometer and said mass filter.

54. A mass spectrometer comprising:
an ion source;
a mass filter;
an ion mobility spectrometer arranged downstream of said mass filter; and
a mass analyser;
wherein said mass filter and said ion mobility spectrometer are operated, in use, so that doubly and/or other multiply charged ions are transmitted to said mass analyser and singly charged ions are attenuated.

* * * * *